US011738756B2

(12) United States Patent
Gray et al.

(10) Patent No.: US 11,738,756 B2
(45) Date of Patent: Aug. 29, 2023

(54) FACIAL RECOGNITION AND MONITORING DEVICE, SYSTEM, AND METHOD

(71) Applicant: MOMENT AI, INC., Memphis, TN (US)

(72) Inventors: Megan Gray, Memphis, TN (US); Jacob Sutton, Bowling Green, KY (US)

(73) Assignee: Moment AI, Inc., Memphis, TN (US)

( * ) Notice: Subject to any disclaimer, the term of this patent is extended or adjusted under 35 U.S.C. 154(b) by 0 days.

(21) Appl. No.: 17/621,554

(22) PCT Filed: Jun. 30, 2020

(86) PCT No.: PCT/US2020/040327
§ 371 (c)(1),
(2) Date: Dec. 21, 2021

(87) PCT Pub. No.: WO2021/003172
PCT Pub. Date: Jan. 7, 2021

(65) Prior Publication Data
US 2022/0363265 A1 Nov. 17, 2022

Related U.S. Application Data

(60) Provisional application No. 62/868,953, filed on Jun. 30, 2019.

(51) Int. Cl.
B60W 40/08 (2012.01)
B60W 60/00 (2020.01)
(Continued)

(52) U.S. Cl.
CPC ............... *B60W 40/08* (2013.01); *A61B 5/18* (2013.01); *B60Q 1/46* (2013.01); *B60Q 1/52* (2013.01);
(Continued)

(58) Field of Classification Search
CPC ............ B60W 40/08; B60W 60/0016; B60W 2040/0818; B60W 2420/42;
(Continued)

(56) References Cited

U.S. PATENT DOCUMENTS 9,412,273 B2 * 8/2016 Ricci .................... B60R 16/037
10,657,825 B2 * 5/2020 Oshida ................ B60W 30/165
(Continued)

OTHER PUBLICATIONS

International Search Report for International Application PCT/US20/040327, dated Sep. 29, 2020.

*Primary Examiner* — Mohamed Barakat
(74) *Attorney, Agent, or Firm* — The Dobrusin Law Firm, P.C.; Daniela M. Thompson-Walters

(57) ABSTRACT

The present teachings relate to a device, system, and method for facial recognition and monitoring. The present teachings may relate to a method for recognizing and monitoring one or more users for an occurrence of a health event of the one or more users comprising: a) receiving incoming video data; b) preprocessing the video data; c) extracting facial data to identify one or more users; d) recognizing the presence, probability, and/or absence of the health event; e) generating one or more notifications or not generating based on the presence, probability, and/or absence of the health event; and f) optionally, enabling one or more safety protocols of a vehicle.

20 Claims, 10 Drawing Sheets

(51) Int. Cl.
*G06V 40/16* (2022.01)
*G06V 20/40* (2022.01)
*G06V 10/82* (2022.01)
*G06V 20/59* (2022.01)
*B60Q 1/50* (2006.01)
*A61B 5/18* (2006.01)
*B60Q 1/46* (2006.01)
*B60Q 1/52* (2006.01)

(52) U.S. Cl.
CPC ......... *B60Q 1/544* (2022.05); *B60W 60/0016* (2020.02); *G06V 10/82* (2022.01); *G06V 20/46* (2022.01); *G06V 20/597* (2022.01); *G06V 40/161* (2022.01); *G06V 40/171* (2022.01); *B60W 2040/0818* (2013.01); *B60W 2420/42* (2013.01); *B60W 2540/221* (2020.02); *B60W 2540/26* (2013.01); *B60W 2556/45* (2020.02)

(58) Field of Classification Search
CPC ....... B60W 2540/221; B60W 2540/26; B60W 2556/45; A61B 5/18; B60Q 1/46; B60Q 1/52; B60Q 1/544; G06V 10/82; G06V 20/46; G06V 20/597; G06V 40/161; G06V 40/171
See application file for complete search history.

(56) References Cited

U.S. PATENT DOCUMENTS

| | | | |
|---|---|---|---|
| 2008/0291008 A1* | 11/2008 | Jeon | G06V 10/95 340/539.1 |
| 2015/0092056 A1* | 4/2015 | Rau | B60R 11/04 348/148 |
| 2018/0126901 A1* | 5/2018 | Levkova | B60W 40/09 |
| 2019/0071055 A1* | 3/2019 | Luchner | B60R 25/25 |
| 2020/0269848 A1* | 8/2020 | Kang | G06N 20/00 |

* cited by examiner

FACIAL RECOGNITION AND MONITORING DEVICE, SYSTEM, AND METHOD

FIELD

The present teachings relate to a device, system, and method for facial recognition and monitoring. The present teachings may find particular use within vehicles. Using facial recognition and monitoring, the device, system, and method may be particularly useful in identifying irregular health events associated with health conditions of a driver and/or passengers and initiating safety functions of a vehicle and/or mobile device upon the identification of the irregular health events.

BACKGROUND

Traffic accident injuries are the world's 8$^{th}$ leading cause of death, killing approximately 1.35 million people each year, and affecting an additional 20-50 million people with non-fatal injuries or disabilities. In the United States alone, approximately 6 million accidents occur each year, 90% of which can be attributed to incorrect driver and/or operator decisions. As modern consumer technology continues to advance, drivers and/or operators are becoming increasingly error-prone while driving, which may be partially attributed to the use of distracting, hand-held devices. These driver and/or operator errors may be referred to as regular events which impact driving conditions.

In addition to traffic accidents related to driver and/or operator decisions, the quick onset of an irregular health event related to a medical condition of a driver and/or passenger may result in unsafe operating conditions. An irregular health event of a driver may quickly impact a driver's ability to safely operate a vehicle. An irregular health event of a passenger may quickly impact a driver's emotions and attention, also impacting a driver's ability to safely operate a vehicle. An irregular health event may be associated with a medical condition of which an individual may have no control, no knowledge in advance of the upcoming onset, or both. Some medical conditions, such as epilepsy, may be associated with frequent or infrequent irregular health events and may even limit the ability of an individual to obtain a driver's license, due to the uncertainty and likelihood of the occurrence of the irregular health event.

What is needed is a device, system, and method which may be able to detect one or more regular events, irregular health events, or both. What is needed is a device, system, and method which may be able to be used within a vehicle. What is needed is a device, system, and method which may be able to identify a regular event, an irregular health event, or both in one or more drivers, passengers, or both. What is needed is a device, system, and method which may be able to provide a driver, with one or more medical conditions which may impact driving, the ability to drive a vehicle safely. What is needed is a device, system, and method which may be able to cooperate with a mobile device, in-vehicle communication system, or both to contact one or more emergency services, pre-identified contacts, or a combination thereof. What is needed is a device, system, and method which may be able to cooperate with a driver assistance technology such that a vehicle is able to execute one or more emergency protocols. What is needed is a device, system, and method which may be able to cooperate with a vehicle to reduce the likelihood of a traffic incident associated with a regular event, irregular health event, or both.

SUMMARY

The present teachings relate to a method for detecting an occurrence of an irregular health condition of one or more users comprising: a) receiving incoming video data by one or more processors related to the one or more users; b) preprocessing the video data by the one or more processors into frame data, wherein the frame data includes one or more single frames, batches of frames, sequence of frames, or a combination thereof; c) extracting facial data by the one or more processors from the frame data to identify the one or more users, wherein the facial data includes one or more extracted faces, numeric array representations of faces of the one or more users, one or more measurements and/or predictions of one or more poses of the one or more users, or a combination thereof; d) determining the presence, probability, absence, or any combination thereof of the irregular health condition in the one or more users by the one or more processors by comparing the facial data with one or more stored facial data models accessible by the one or more processors; e) generating one or more notifications based on recognizing the presence and/or probability of the irregular health condition or not generating a notification based on the absence of the irregular health condition; and f) optionally, upon recognizing the presence and/or probability of the irregular health condition, transmitting one or more emergency signals from the one or more processors to a vehicle to enable driver assistance technology to control driving of the vehicle in which the one or more users are located, such that the vehicle drives to and reaches a safe parking destination and/or turns on one or more emergency notifiers of the vehicle.

The present teachings may provide for a system for facial recognition and monitoring comprising i) one or more cameras; and ii) one or more image processing units in communication with the one or more cameras, including: a) one or more processors, b) one or more graphics processors, c) one or more memory storage devices, and d) one or more network connections. The one more image processing units and one or more cameras may be part of a recognition device.

The present teachings provide a device, system, and method which may be able to detect one or more health events. The health events may include one or more regular events, irregular events or both. The presenting teachings provide a system which may be preprogrammed by one or more humans, trained using one or more machine learning training models, or both. The system may be provided with one or more video streams, images, and/or frames of a plurality of users experiencing one or more health events. Using facial recognition and machine learning, the system may be able to learn one or more facial recognition traits associated with one or more health events. The present teachings provide a device, system, and method which may utilize a facial recognition and monitoring method (FRM method) to determine the presence and/or absence of one or more health events in a user. The FRM method of the present teachings may be useful in identifying the health event. The present teachings may provide a recognition device which may be able to be integrated into a vehicle. The present teachings may provide a system which is compatible with a mobile device of a user. Thus, whether the user is using a recognition device or mobile device, they user may be able to execute at least a portion of FRM method while in a vehicle or any other setting. The present teachings provide a system which may be compatible with one or more controls of the vehicle, mobile device, or both. The present teachings may provide a system which is able to communicate with the vehicle, mobile device, or both and execute one or more safety protocols. The safety protocols may allow for a vehicle to initiate vehicle assistance technology to maneuver a vehicle into a safer position. The safety protocols may include initiating contact with emergency services, pre-identified contacts, or both to alert and/or send for assistance for the user if they are experiencing a health event.

The present teachings may provide an unconventional approach at recognizing and monitoring users via facial recognition, as not only does the system monitor a user's behavior, but also their health conditions. Furthermore, typical systems may function to alert a driver of a conscious behavior while driving so as to refocus the attention of the driver to the road and surrounding driving conditions to adequately control the vehicle. The present teachings provide a device, system, and method for not only identifying irregular health events which may be unpredicted and not under the control of the user, but even compensating when a driver is unable to maintain control of a vehicle due to the severity of a health event.

DETAILED DESCRIPTION

Figure 1:
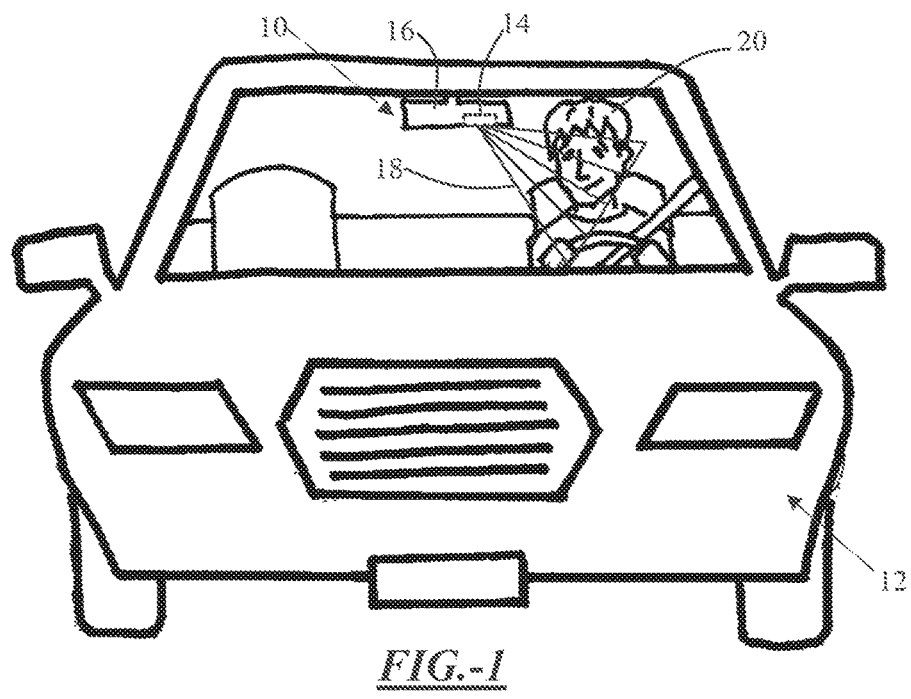
FIG. 1 illustrates a recognition device integrated into a vehicle according to the teachings herein.

The explanations and illustrations presented herein are intended to acquaint others skilled in the art with the present teachings, its principles, and its practical application. The specific embodiments of the present teachings as set forth are not intended as being exhaustive or limiting of the present teachings. The scope of the present teachings should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Setting(s) for Facial Recognition and Monitoring System and Method

The facial recognition and monitoring system and method of the present teachings may be found useful in multiple settings. Settings may include within one or more vehicles, residential settings (e.g., homes), education settings (e.g., classrooms), medical settings (e.g., hospitals), the like, or a combination thereof. The system and method may be advantageous for use within vehicles to not only identify the presence of one or more human conditions, but also activating one or more emergency features of the vehicle to maintain safety of the driver, passengers, and other vehicles and individuals in proximity of the vehicle. One or more vehicles may include one or more private passenger vehicles, public passenger vehicles, or both. One or more private passenger vehicles may include one or more automobiles, boats, bicycles, motorcycles, wheelchairs, small passenger planes, helicopters, recreational vehicles (e.g., RV, ATV, OTV), the like, or a combination thereof. One or more automobiles may include one or more cars, trucks, sports utility vehicles, cross-over vehicles, the like, or any combination thereof. One or more public passenger vehicles may include one or more buses, trains, boats, planes, chairlifts, the like, or any combination thereof. The one or more settings may be suitable for at least temporarily accommodating one or more users.

The facial recognition and monitoring system and method of the present teachings may be employed by one or more users. One or more users may include a single user or a plurality of users. One or more users may be within the same setting or different settings. One or more users may include one or more humans, animals, or both. One or more animals may include one or more domestic pets, wild animals, the like, or any combination thereof. The one or more users may include one or more drivers, passengers, or both of one or more vehicles. The one or more users may have one or more known health conditions or may be free or one or more health conditions. The one or more users may be aware and/or unaware of the presence of one or more health conditions.

Health Condition and Health Event

The facial recognition and monitoring system and method of the present teachings may find particular use in identifying the occurrence of one or more health events. The one or more health events may include one or more health events that may make driving and/or being a passenger in a vehicle at least temporarily unsafe for one or more passengers, drivers, or both of the same vehicle, other vehicles in proximity, other individuals in proximity to the user (e.g., pedestrian), the like, or any combination thereof. The one or more health events may include one or more events in which the ability to focus on driving, to physically control driving of the vehicle, or both may be at least temporarily impaired. The one or more health events may include one or more irregular health events, regular events, or both.

One or more health events may include one or more irregular health events. One or more irregular health events may be tied to one or more medical conditions, behaviors, or both of one or more users. One or more irregular health events may be unable to be controlled by a user once the event is occurring. One or more irregular health events may include one or more health conditions with a quick onset, slow onset, no known symptoms in advance, spontaneous occurrence, the like, or any combination thereof. One or more irregular health events may be a result of a behavior of one or more users, may be known to result by one or more users, or both. One or more irregular health events may be one or more health events of which a user (e.g., individual) may have no control, knowledge of an upcoming onset, or both. One or more irregular health events may include one or more seizures, heart attacks, strokes, fainting, falling asleep, drowsiness, inebriation, vomiting, the like, or any combination thereof. One or more health conditions may include epilepsy, high cholesterol, high blood pressure, aneurysm, pregnancy, narcolepsy, dehydration, the like, or any combination thereof. One or more behaviors may include alcohol consumption, drug consumption, lack of sleep, the like, or any combination thereof.

In addition to irregular events, regular events may be experienced by a user which may make the driving experience unsafe. Regular events may be those which may be caused by a user, the user is consciously and/or subconsciously aware of, the user may consciously choose to engage in, the like, or any combination thereof. Regular events may include heightened emotions (e.g., anger toward a fellow passenger, sadness at a personal situation etc.), attention or lack thereof to the road and driving conditions (e.g., engaging in deep conversation with a fellow passenger), looking away from the road, driving habits (e.g., tendency to speed or tailgate while angry or stressed), texting and/or otherwise looking at a mobile device, the like, or any combination thereof.

The one or more users may be recognized and monitored by a recognition device.

Recognition Device

The present teachings may relate to a recognition device. The recognition device may be useful in recognizing and monitoring one or more users, such as in one or more settings. The recognition device may be useful for locating within one or more settings. The recognition device may be temporarily, semi-permanently, and/or permanently affixed and/or located within a setting. For example, a recognition device may be permanently affixed within a vehicle. As another example, a recognition device may be temporarily or semi-permanently affixed within a vehicle. A recognition device may be located within any portion of a vehicle in which one or more cameras may have line of sight on one or more users within the vehicle. The one or more users may include one or more drivers, passengers, or both. The recognition device may be at least partially located on a rearview mirror, headliner, steering wheel, visor, instrument panel, entertainment center, internal vehicle control, passenger seats, headrests, panels (e.g., doors) within a vehicle, door trim, pillars (e.g., A, B, and/or C-pillar), consoles (e.g., center console), the like, or any combination thereof. The recognition device may include one or more housings. A housing may function to retain one or more components of the recognition device. A housing may be permanently, semi-permanently, or not affixed to one or more portions of a vehicle or within other settings. For example, a housing may be permanently located within an instrument panel of a vehicle. As another example, a housing may be temporarily attached to any interior portion of a vehicle (e.g., mounting hardware, suction cups, hooks, the like, or any combination thereof. As another option, a housing may rest within a holder of a vehicle. For example, a cup holder, tray, and the like within the vehicle. The recognition device may include one or more sensing devices (e.g., cameras), sensing device connections, sensing device modules, image processing units, processors, memory storage devices, housings, applications, network connections, power supplies, the like, or any combination thereof.

The recognition device may include one or more viewer sensing devices. The one or more sensing devices may function to detect the presence of a user, recognize a user, monitor a user, the like, receive and/or transmit data related to the user, or any combination thereof. The one or more sensing devices may include one or more cameras, motion sensors, heart rate monitors, breathing monitors, the like, or any combination thereof. One or more sensing devices may include one or more cameras (e.g., camera modules). The one or more cameras may be suitable for capturing one or more videos, images, frames, the like, or any combination thereof. The one or more cameras may be positioned within a setting to have a line of sight on one or more users. Line of sight may mean the camera is in view of at least part of or all of a person's face, at least part of or all of a person's body (e.g., upper torso, arms, shoulders, etc.), or any combination thereof. Line of sight may mean having the user's eyes, nose, mouth, ears, neck, or any combination thereof in view of the camera. The one or more cameras may have a line of sight (e.g., have in view) a single user or a plurality of users. For example, a camera may be positioned in a vehicle to have a line of sight on a face of a driver. As another example, a camera may be positioned in a vehicle to have a line of sight on a face of a passenger in the front passenger seat. As a further example, a camera may be positioned in a vehicle to have a line of sight on the faces of passengers in rear passenger seats of a vehicle. The camera may point toward a rear, side, and/or front of a vehicle. Pointing generally toward a rear of a vehicle will provide for one or more front-facing users to have their face(s) within the line of sight of the camera. The recognition device may be free of one or more sensing devices and be in communication with one or more sensing devices. The one or more cameras may have a wide-angle lens (e.g., viewing angle of 150 degrees or greater). The one or more cameras may be capable of capturing static images, video recordings, or both at resolutions of about 480 pixels or greater, 640 pixels or greater, 720 pixels or greater, or even 1080 pixels or greater. The one or more cameras may be able to capture video recordings at a frame rate of about 25 frames per second or greater, about 30 frames per second or greater, about 60 frames per second or greater, or even 90 frames per second or greater. A suitable camera for use with the recognition device may include the SainSmart IMX219 Camera Module with an 8MP sensor and 160-degree field of vision, the camera module and its specifications incorporated herein by reference for all purposes.

The recognition device may include or be connectable with one or more sensing device connections. The one or more sensing device connections may function to connect one or more sensing devices to the recognition device, an image processing unit, a power supply, the like, or any combination thereof. The one or more sensing device connections may be wired, wireless, or both. The one or more sensing device connections may include one or more communication wires connecting one or more sensing devices to one or more image processing units. For example, the one or more sensing device connections may include a wire connecting a camera (e.g., camera module) to an image processing unit. The one or more sensing device connections may be any type of cable and or wire suitable for transferring data including video, images, frames, sound, the like, or any combination thereof. The one or more sensing device connections may allow for one or more sensing devices to be located within a passenger area of a vehicle while the image processing unit is located within a controls section of a vehicle such that they are separate from one another. The one or more sensing device connections may allow for one or more sensing devices to be located within a same housing as an image processing unit.

The recognition device may include one or more image processing units. One or more image processing units may function to receive, process, transmit image data, or any combination thereof; store image data; or both. The one or more image processing units may include one or more processors, memory storage devices, circuit boards, the like, or any combination thereof. The one or more image processing units may include one or more central processing units, graphics processing units, memory mediums, storage mediums, the like, or any combination thereof. The one or more image processing units may include an electronic circuit board or similar. The electronic circuit board may house and place one or more processing units and memory storage devices in communication with one another. The electronic circuit board may be in communication with one or more sensing device modules, power supply sources, network connections, the like, or any combination thereof. The electronic circuit board may be located within a housing of a recognition device. The electronic circuit board may be housed in a same or different housing as one or more sensing devices.

The one or more image processing units may include one or more processors. One or more processors may function to analyze image data, execute instructions, transmit image data, or any combination thereof. The one or more processors may be located within the recognition device. The one or more processors may be located within a same or separate housing as one or more sensing devices. The one or more processors may include a single or a plurality of processors. The one or more processors may function to process data, execute one or more instructions to analyze data, or both. Processing data may include receiving, transforming, outputting, executing, the like, or any combination thereof. One or more processors may be in communication with one or more memory storage devices. One or more processors may access and execute one or more instructions stored within one or more memory mediums. One or more processors may store processed data within one or more storage mediums. One or more processors may be part of one or more hardware, software, systems, or any combination thereof. The one or more processors may be referred to as one or more electronic processors. One or more hardware processors may include one or more central processing units, multi-core processors, front-end processors, graphics processors, the like, or any combination thereof. One or more processors may include one or more central processing units (CPU), graphics processing units (GPU), or both. One or more processors may be in communication with, work together with, or both one or more other processors. For example, a central processing unit may cooperate with a graphics processing unit. One or more processors may be a processor, microprocessor, electronic circuit, the like, or a combination thereof. For example, a central processing unit may be a processor or microprocessor. A central processing unit may function to execute instructions stored within a memory medium of the recognition device. An exemplary central processing unit may include the Cortex-A57 processor provided by Arm Limited, the processor and its specifications incorporated herein by reference for all purposes. As an example, a graphics processing unit may include one or more electronic circuits. A graphics processing unit may function to accelerate creation and rendering of image data. Image data may include images, videos, animation, frames, the like, or a combination thereof. The graphics processing unit may be beneficial in performing fast math calculations associated with the image data and freeing up processing capacity of the central processing unit. An exemplary graphics processing unit may include the GeForce® GTX 1650 D6 0C Low Profile 4G (model number GV-N1656OC-4GL) by GIGA-BYTE Technology Co., the module and its specifications incorporated herein by reference. The one or more processors may be non-transient. The one or more processors may convert incoming data to data entries to be saved within one or more storage mediums.

One or more image processing units may include one or more memory storage devices (e.g., electronic memory storage device). The one or more memory storage devices may function to store data, databases, instructions, or any combination thereof. The one or more memory storage devices may include one or more hard drives (e.g., hard drive memory), chips (e.g., Random Access Memory "RAM)"), discs, flash drives, memory cards, the like, or any combination thereof. One or more discs may include one or more floppy diskettes, hard disk drives, optical data storage media including CD ROMs, DVDs, and the like. One or more chips may include ROMs, flash RAM, EPROMs, hardwired or preprogrammed chips, nanotechnology memory, or the like. The data stored within one or more memory storage devices may be compressed, encrypted, or both. The one or more memory storage devices may be located within a recognition device. One or more memory storage devices may be non-transient. One or more memory storage devices may include one or more memory mediums, storage mediums, the like, or a combination thereof. One or more memory mediums may store one or more computer executable instructions. One or more memory mediums may store one or more algorithms, methods, rules, the like, or any combination thereof. One or more memory mediums may be accessible by one or more processors (e.g., CPU, GPU) to read and/or execute one or more computer executable instructions. An exemplary memory medium may include the Kingston ValueRAM 4 GB DDR SDRAM Memory Module, the memory module and its specifications incorporated herein by reference. One or more storage mediums may store one or more databases. One or more storage mediums may store one or more algorithms, methods, rules, the like, or a combination thereof. One or more storage mediums may store one or more computer executable instructions. Instructions, algorithms, methods, rules, and the like may be transferred from one or more storage mediums to one or more memory mediums for accessing and execution by one or more processors. One or more storage mediums may store one or more data entries in a native format, foreign format, or both. One or more storage mediums may store data entries as objects, files, blocks, or a combination thereof. One or more storage mediums may store data in the form of one or more databases. One or more storage mediums may store data received from one or more processors (e.g., CPU, GPU). One or more storage mediums may store data received from one or more processors after the one or more processors execute one or more instructions from one or more memory mediums. An exemplary storage medium may include the 16 GN eMMC Module XU4 Linux sold by HardKernel Co., Ltd., the module and its specifications incorporated herein by reference.

The recognition device may include one or more power supplies. A power supply may function to provide electric power to an electrical load of a recognition device, transmit power to an image processing unit, or both. A power supply may be any device capable of converting electric current from a power source to a correct voltage, current, and/or frequency to power the electrical load of the recognition device. A power supply may be located in the same or a different housing as an image processing unit. A power supply may have one or more power input connections, power output connections, or both. A power input connection may function to connect to a power input, receive energy in the form of electric current from a power source, or both. A power source may include an electrical outlet, energy storage devices, or other power supplies. A power source may be a power source of a vehicle. A power source may include one or more batteries, fuel cells, generators, alternators, solar power converters, the like, or any combination thereof. A power output connection may function to connect to one or more electric components of a recognition device, connect to an image processing unit, delivery current to one or more electrical loads of the recognition device, or any combination thereof. The power input connection, power output connection, or both may be wired (e.g., hardwired circuit connection) or wireless (e.g., wireless energy transfer). An exemplary power supply may be the RS-15-24 single output switching power supply by MEAN WELL which is an AC/DC 15 W 24V single output power supply, the power supply and its specifications incorporated herein by reference.

The recognition device may include one or more network connections. The one or more network connections may function to place the recognition device in communication with one or more networks. The one or more network connections may be in communication with and/or connected to one or more image processing units. The one or more network connections may be in communication with one or more networks. The one or more network connections may be suitable for connecting to the Internet. The one or more network connections may include one or more IoT (i.e., "Internet of Things) connections. The one or more network connections may be wired, wireless, or both. An exemplary network connection may include the INP 1010/1011 multi-protocol wireless module provided by InnoPhase, the module and its specifications incorporated herein by reference.

The recognition device may include one or more application layers. The one or more application layers may function to retain one or more facial recognition and monitoring methods, provide accessible computer executable instructions, be accessible by one or more image processing units, the like, or any combination thereof. The one or more application layers may be software (e.g., computer executive instructions). The one or more application layers may be in communication with one or more networks. The one or more application layers may be able to be created, updated, or otherwise modified remotely via one or more networks and one or more network connections.

Facial Recognition and Monitoring System ("FRM System")

The FRM system may include one or more physical data centers. A physical data center may function to house one or more components of the FRM system. The physical data center may function to host one or more servers, processors, memory storage devices, networks, the like, or any combination thereof. The physical data center may function to provide a non-transient host location for one or more components of the FRM system. The physical data center may include at about 1 terabyte of storage space or greater, about 2 terabytes of storage space or greater, or even 5 terabytes of storage space or greater. The physical data center may operate one or more components on one or more operating systems. One or more operating systems may include Linux, Windows, MacOS, ArcaOS, Haiku, ReactOS, FreeDOS, Wayne OS, the like, or any combination thereof. The physical data center may function to host one or more modules, execute one or more modules, or both of a cloud-based network.

The system may include one or more processors. The one or more processors may function to analyze one or more data from one or more sensing devices, memory storage devices, databases, user interfaces, recognition devices, modules, the like or any combination thereof; convert one or more incoming data signals to data suitable for analysis and/or saving within a database (e.g., data conversion, data cleaning); or a combination thereof. One or more processors may be included in one or more user interfaces, servers, computing devices, the like, or any combination thereof. The one or more processors may or may not be cloud-based (e.g., remote from other portions of the system). One or more processors hosted by a physical data center may be considered cloud-based. One or more processors hosted remotely from one or more recognition devices, personal computing devices, or both may be considered cloud-based. One or more processors may include a single or a plurality of processors. One or more processors may be in communication with one or more other processors. One or more processors may be associated with and/or execute one or more modules of one or more systems. The one or more processors may function to process data, execute one or more algorithms to analyze data, or both. Processing data may include receiving, transforming, outputting, executing, the like, or any combination thereof. One or more processors may be part of one or more hardware, software, systems, or any combination thereof. One or more hardware processors may include one or more central processing units, multi-core processors, front-end processors, graphics processing units, the like, or any combination thereof. The one or more processors may be non-transient. The one or more processors may be referred to as one or more electronic processors. The one or more processors may convert data signals to data entries to be saved within one or more memory storage devices. The one or more processors may access one or more algorithms (e.g., computer executable instructions) saved within one or more memory storage mediums.

The system may include one or more memory storage devices (e.g., electronic memory storage device). The one or more memory storage devices may store data, databases, algorithms, processes, methods, or any combination thereof. The one or more memory storage devices may include one or more hard drives (e.g., hard drive memory), chips (e.g., Random Access Memory "RAM"), discs, flash drives, memory cards, the like, or any combination thereof. One or more discs may include one or more floppy diskettes, hard disk drives, optical data storage media including CD ROMs, DVDs, and the like. One or more chips may include ROMs, flash RAM, EPROMs, hardwired or preprogrammed chips, nanotechnology memory, or the like. The one or more memory storage devices may include one or more cloud-based storage devices. One or more memory storage devices located remote from one or more recognition devices, personal computing devices, and/or user interfaces, may be considered a cloud-based storage device. The data stored within one or more memory storage devices may be compressed, encrypted, or both. The one or more memory storage devices may be located within one or more computing devices, servers, processors, user interfaces, or any combination thereof. One or more memory storage devices may be referred to as one or more electronic memory storage devices. One or more memory storage devices may be non-transient. One or more memory storage mediums may store one or more data entries in a native format, foreign format, or both. One or more memory storage mediums may store data entries as objects, files, blocks, or a combination thereof. The one or more memory storage mediums may include one or more algorithms, methods, rules, databases, data entries, the like, or any combination thereof stored therein. The one or more memory storage mediums may store data in the form of one or more databases.

One or more computing devices may include one or more databases. The one or more databases may function to receive, store, and/or allow for retrieval of one or more data entries. Data entries may be one or more video streams, frames, identifiers, frame analysis results, user data, and the like associated with one or more users. The one or more databases may be located within one or more memory storage devices. The one or more databases may include any type of database able to store digital information. The digital information may be stored within one or more databases in any suitable form using any suitable database management system (DBMS). Exemplary storage forms include relational databases (e.g., SQL database, row-oriented, column-oriented), non-relational databases (e.g., NoSQL database), correlation databases, ordered/unordered flat files, structured files, the like, or any combination thereof. The one or more databases may store one or more classifications of data models. The one or more classifications may include column (e.g., wide column), document, key-value (e.g., key-value cache, key-value store), object, graph, multi-model, or any combination thereof. One or more databases may be located within or be part of hardware, software, or both. One or more databases may be stored on a same or different hardware and/or software as one or more other databases. One or more databases may be located in a same or different non-transient storage medium as one or more other databases. The one or more databases may be accessible by one or more processors to retrieve data entries for analysis via one or more algorithms, methods, rules, processes, or any combination thereof. The one or more databases may include a single database or a plurality of databases. One database may be in communication with one or more other databases. One or more other databases may be part of or separate from the system. One or more databases may be connected to one or more other databases via one or more networks. Connection may be wired, wireless, the like, or a combination thereof. For example, a database of the system may be in communication with one or more other databases via the Internet. The database may also receive one or more outputs of the system. The database may be able to have the data outputted, sorted, filtered, analyzed, the like, or any combination thereof. The database may be suitable for storing a plurality of records.

The system may include one or more applications. The application (i.e., "computer program") may function to access data, upload data, or both to the FRM system, interaction with a user interface, or any combination thereof. The application may be stored on one or more memory storage devices. The application may be stored on one or more personal computing devices. The application may comprise and/or access one or more computer-executable instructions, algorithms, rules, processes, methods, user interfaces, menus, databases, the like, or any combination thereof. The computer-executable instructions, when executed by a computing device may cause the computing device to perform one or more methods described herein. The application may be downloaded, accessible without downloading, or both. The application may be downloadable onto one or more computing devices. The application may be downloadable from an application store (i.e., "app store"). An application store may include, but is not limited to, Apple App Store, Google Play, Amazon Appstore, or any combination thereof. The applicable may be accessible without downloading onto one or more computing devices. The application may be accessible via one or more web browsers. The application may be accessible as a website. The application may interact and/or communication through one or more user interfaces. The application may be utilized by one or more computing devices. The application may be utilized on one or more computing devices. The application may also be referred to as a dedicated application.

One or more computing devices (e.g., personal computing devices) may include one or more user interfaces. The one or more user interfaces may function to display information related to a user, receive user inputs related to a user, display data and/or one or more prompts to a user, or any combination thereof. The one or more user interfaces may be suitable for receiving data from a user. The one or more user interfaces may include one or more graphic user interfaces (GUI), audio interfaces, image interfaces, the like, or any combination thereof. One or more graphic user interfaces may function to display visual data to a user, receive one or more inputs from the user, or both. The one or more graphic interfaces may include one or more screens. The one or more screens may be a screen located on a computing device. The one or more screens may be a screen on a mobile computing device, non-mobile computing device, or both. The one or more graphic interfaces may include and/or be in communication with one or more user input devices, audio interfaces, image interfaces, the like, or any combination thereof. The one or more user input devices may allow for receiving one or more inputs from a user. The one or more input devices may include one or more buttons, wheels, keyboards, switches, mice, joysticks, touch pads (i.e., a touch-sensitive area, provided as a separate peripheral or integrated into a computing device, that does not display visual output), touch-sensitive monitor screens, microphones, the like, or any combination thereof. The one or more input devices may be integrated with a graphic user interface. An audio interface may function to project sound to a user and/or receive sound from a user. The audio interface may include audio circuitry, one or more speakers, one or more microphones, the like, or any combination thereof. An image interface may function to capture, receive, display, and/or transmit one or more images. An image interface may include one or more cameras. A user interface may function to display and/or navigate through one or more menus of the application.

The system may include one or more computing devices. The one or more computing devices may function to allow a user to interact with an application, the system, or both; execute one or more algorithms, methods, and/or processes; receive and/or transmit one or more signals, convert one or more signals to data entries, retrieve one or more data entries from one or more storage mediums, or any combination thereof. The one or more computing devices may include and/or be in communication with one or more processors, memory storage devices, servers, networks, user interfaces, recognition devices, other computing devices, the like, or any combination thereof. The one or more or more computing devices may be in communication via one or more interaction interfaces (e.g., an application programming interface ("API")). The computing device may be one or more personal computers (e.g., laptop or desktop), mobile devices (e.g., mobile phone, tablet, smart watch, etc.), or any combination thereof. The computing device may include one or more personal computing devices. Personal computing devices may be computing devices typically used be a single person, having a log-in or sign-in function or other user authentication, can store and relay information privately to a user, the like, or a combination thereof. Personal computing devices may have the ability to transmit one or more notifications to one or more emergency services, predetermined contacts, the like, or a combination thereof. Personal computing devices may have the ability to send and/or receive one or more text messages, SMS messages, push notifications, emails, phone calls, the like, or any combination thereof.

The system of the present disclosure may be integrated and/or include one or more networks. The physical data center, one or more user interfaces, one or more personal computing devices, one or more recognition devices, one or more cloud networks, or any combination thereof may be in selective communication with one or more networks. The one or more networks may be formed by placing two or more computing devices in communication with one another. One or more networks may include one or more physical data centers, communication hubs, communication modules, computing devices, processors, databases, servers, memory storage devices, recognition devices, sensing devices, the like, or any combination thereof. One or more networks may be free of and/or include one or more communication hubs (e.g., router, wireless router). One or more components of the system may be directly connected to one another without the use of a communication hub. One or more networks may be connected to one or more other networks. One or more networks may include one or more local area networks ("LAN"), wide area networks ("WAN"), virtual private network ("VPN"), intranet, Internet, cellular networks, the like, or any combination thereof. The network may be temporarily, semi-permanently, or permanently connected to one or more computing devices, recognition devices, user interfaces, the like, or any combination thereof. A network may allow for one or more computing devices, recognition devices, user interfaces, physical data centers, or a combination thereof to be connected to one or more portions of the system, transmit data between one or more components of the system, or any combination thereof. One or more portions of the network hosted at one or more physical data centers may form one or more cloud-based network, recognition device management networks, video stream management network, the like, or any combination thereof.

The system may include one or more recognition device management networks. The one or more recognition device management networks may function to receive and collect data from one or more recognition devices. The one or more recognition device management networks may be at least partially hosted by the same or different physical data centers as the cloud-based network, video stream management network, or both. The one or more recognition device management networks may include one or more remote storage devices, recognition devices, processors, or a combination thereof. The one or more remote storage devices may include one or more main storage devices, node storage devices, or both. One or more node storage devices may be layered between and in communication with both a plurality of recognition devices and a main storage device. One or more node storage devices may function to predetermined data from a plurality of recognition devices. Each node storage device may be associated with a different set of predetermined data from the same or different recognition devices as another node storage device. The node storage devices may organize collected data into groups. For example, one node storage device may collect data for users in public transportation vehicles. As another example, one node storage device may collect data associated with users in private passenger vehicles. As a further example, one node storage device may collect data for users of ages 20-29 while another collected data for users ages 30-39 (e.g., nodes assigned by age of users). The one or more node storage devices may append one or more identifiers to collected data (e.g., unique identifiers), collect all data output received from a recognition device or both. The one or more node storage devices may transmit collected data to one or more main storage devices.

The system may include one or more video stream management networks. The one or more video stream management networks may function to receive and collect data from one or more personal computing devices, web servers, user interfaces, the like, or any combination thereof. The one or more video stream management networks may be at least partially hosted by the same or different physical data centers as the cloud-based network, recognition device management network, or both. The one or more video stream management networks may include one or more remote storage devices, processors, personal computing devices, web servers, or any combination thereof. The one or more video stream management networks may include one or more video stream clouds. One or more video stream clouds may include one or more memory storage devices, processors, web servers, the like, or a combination thereof. One or more video stream clouds may include video data stored therein. Video data may include one or more video streams, image data, frames, the like, or a combination thereof stored therein. One or more video stream clouds may associate one or more uniform resource locators (URL) to one or more video data files. Each video data file stored within a video stream cloud may be associated with its own URL. The one or more video stream clouds may be provided by a video streaming and hosting services within or remotely accessible to the cloud-based network, one or more personal computing devices, or both. The one or more video stream clouds may be configured to accept video streams using Real Time Streaming Protocol (RTSP), Internet Protocol (IP), the like, or a combination thereof. The video streams may be received by the video stream cloud from one or more user video clouds, user data centers, or both. A video stream cloud may be video cloud storage (e.g., remote storage) for videos of a specific user. For example, a user may have their own user authentication to log in to and save video stream files into their video stream cloud. A user data center may be a computing device of a user which is able to store video data internally.

The one or more remote storage devices may include one or more main storage devices, node storage devices, or both. One or more node storage devices may be layered between and in communication with both a plurality of recognition devices and a main storage device. One or more node storage devices may function to predetermined data from a plurality of recognition devices. Each node storage device may be associated with a different set of predetermined data from the same or different recognition devices as another node storage device. The node storage devices may organize collected data into groups. For example, one node storage device may collect data for users in public transportation vehicles. As another example, one node storage device may collect data associated with users in private passenger vehicles. As a further example, one node storage device may collect data for users of ages 20-29 while another collected data for users ages 30-39 (e.g., nodes assigned by age of users). The one or more node storage devices may append one or more identifiers to collected data (e.g., unique identifiers), collect all data output received from a recognition device or both. The one or more node storage devices may transmit collected data to one or more main storage devices.

A cloud-based network may include one or more device and data management modules, cloud computing and data management modules, features and analytics modules, data storage modules, execution data management modules, development modules, the like, or any combination thereof.

The system may include a device and data management module. The device and data management module may function to collect, organize, and store data received from one or more recognition devices. Data may include video streams, frames, images, sound, frame analysis results, user data, recognition device data, the like, or any combination thereof. The device and data management module may include recognition device event management, recognition device management, and recognition device storage. The device data management module may be in communication, either directly and/or indirectly, with one or more recognition devices. The device data management module may be in communication with one or more remote storage devices. The device data management module collect data from one or more recognition device via recognition device management. Recognition device management may include one or more IoT gateways, connections, and the like. Recognition device management may be any hardware and/or software component suitable for receiving data from one or more recognition devices, remote storage devices, or both. The collected data is then collected and organized by recognition device event management. The recognition device event management may include one or more processors. Recognition device event management may filter and sort collected data from one or more recognition devices. Recognition device event management may sort collected data by users, timestamps, ages of users, genders of users, health events found, geolocations, the like, or any combination thereof. Recognition device management may associate data related to one or more users to one or more user records. Recognition device management may transmit collected and organized data to recognition device storage. Recognition device storage may include one or more memory storage devices. Recognition device storage may include one or more memory mediums, storage mediums, or both. Recognition device storage may include one or more databases. Recognition devices storage may provide for long-term storage, short-term storage, or both. The recognition device storage may transmit collected data to one or more data storage modules. The recognition device storage may transmit collected data to execution storage for long-term storage.

The system may include a cloud computing and data management module. The cloud computing and data management module may function to collect, organize, and store data received from one or more personal computing devices, web servers, the like, or a combination thereof. Data may include video streams, frames, images, sound, frame analysis results, user data, recognition device data, the like, or any combination thereof. The cloud computing and data management module may include a cloud computing module, cloud event management, cloud computing storage, the like, or a combination thereof. The cloud computing module may be in communication, either directly and/or indirectly, with one or more personal computing devise, web servers, the like, or a combination thereof. The cloud computing module may be in communication with one or more remote storage devices. The cloud computing and data management module may collect data from one or more personal computing devices, web servers, remote storage devices, or any combination thereof via the cloud computing module. The cloud computing module may include one or more IoT gateways, connections, and the like. The cloud computing module may include one or more network/IP/S3/RSTP gateways. The cloud computing module may be any hardware and/or software component suitable for receiving data from one or more personal computing devise, web servers, remote storage devices, or both. The collected data is then collected and organized by cloud computing. Cloud computing may include one or more processors. Cloud computing may filter and sort collected data from one or more personal computing devices, web servers, remote storage locations, or a combination thereof. Cloud computing may sort collected data by users, timestamps, ages of users, genders of users, health events found, geolocations, the like, or any combination thereof. Cloud computing may associate data related to one or more users to one or more user records. Cloud computing may transmit collected and organized data to cloud computing storage. Cloud computing storage may include one or more memory storage devices. Cloud computing storage may include one or more memory mediums, storage mediums, or both. Cloud computing storage may include one or more databases. Cloud computing storage may provide for long-term storage, short-term storage, or both. Cloud computing storage may transmit collected data to one or more data storage modules. The cloud computing storage may transmit collected data to execution storage for long-term storage.

The system may include one or more data storage modules. The one or more data storage modules may function to store received data for short-term storage, long-term storage, further analytics, the like, or a combination thereof. One or more data storage modules may include a single or a plurality of storage modules. One or more data storage modules may include execution event storage, cloud storage, execution storage, the like, or a combination thereof. One or more data storage modules may be located within a cloud-based network. One or more data storage modules may include one or more servers, memory storage devise, the like, or a combination thereof. One or more data storage module may include one or more databases stored therein. Execution event storage may provide for an organized record of all detected health events, a portion of detected health events, or both. Organized may mean in chronological sequence from most recent detected event to oldest detected event. A portion of detected health events may be over a predetermined period of time. A period of time may be a predetermined time frame from the present day and back. For example, 6 months, 1 year, 5 years, or even 10 years. Execution storage may provide for long-term storage of data received from recognition device storage, cloud computing storage, or both. Execution storage may be accessible by one or more features and analytics modules. Execution storage may collect data from one or more device and data management modules, cloud computing and data management modules, or both. Execution storage may collect data which includes organized collections of labeled frames, labeled video sequences, extracted data in table format, extracted data in data frames format, other output data from one or more recognition devices, the like, or any combination thereof. Cloud storage may collect data for long-term storage. Cloud storage may collect data from execution storage. Execution storage may incrementally transmit data to cloud storage. Data within cloud storage may enable development improvement and model training within a development module. Cloud storage may be accessible by a development module.

The system may include one or more features and analytics modules. One or more features and analytics modules may provide for one or more user accessible features in an application, obtaining data insights from collected data of a single user or a number of users, or both. One or more features and analytics modules may include a user features and abilities module, data analytics module, execution data management module, or a combination thereof. A user features and abilities module may function to host an application accessible by one or more personal computing devices. A user features and abilities module may allow for user to see their own data (e.g., video streams), trends, detected health events, behaviors, the like, or any combination thereof. A user features and abilities module may allow for a user to see data specific to similar groups, users as a whole, users in certain demographics, and the like. User features and abilities module may access data analytics. Data analytics may execute execution data management. Execution data management may utilize machine learning, artificial intelligence, or both. Execution data management may utilize supervised and/or unsupervised learning. Execution data management may utilize one or more machine learning models. One or more machine learning models may include supervised learning models including linear regression, logistic regression, support vector machine, the like, or a combination thereof. One or more machine learning models may include unsupervised learning models including hierarchal clustering, k-means, self-organizing map, the like, or a combination thereof. One or more machine learning models may allow for effective analysis of user data, extraction of key data trends and insights, or both. Analytics may then be used by the user features and abilities module. The user features and abilities module may allow for trend predictions and data interpretation to provide a concise and comprehensive overview of one or more users' activity. User features and abilities module may provide for real-time alerts, push notifications, and/or displays on user interfaces via one or more personal computing devices.

The system may include a development module. The development module may function to collect and organize data received by the system, provide continuous development improvement and model training, or both. The development module may include a development data management module, data analytics module, development testing module, model and feature development module, the like, or a combination thereof.

The development data management module may collect and organize data for training. The development data module is in communication with one or more storage device modules. The development data module collects and organizes data from cloud storage. The organized data may be referred to as one or more training data sets. One or more training datasets may also be obtained from publicly or privately available datasets which are stored within cloud storage. The development data module enables improvement and training opportunities for current and new models. The models may be located in the model and feature development module. The development data management module may store the collected and organized data within one or more databases. The development data management module may store the collected and organized data within a development cloud training database.

The data analytics module may provide for data insights which can allow for creation and optimization of one or more current or new machine learning models, artificial intelligence models, or both. The data analytics module may include one or more sub-modules. One or more sub-modules may include a visualization module, data analytics generation module, feature extraction module, the like, or a combination thereof. A visualization model may be what enables visualization of the data via one or more user interfaces. A data analytics generation module may provide for detailed analytics. The data analytics generation module may use data from one or more databases, such as a development cloud training database. The data analytics generation module may use machine learning models to analyze the data. The one or more machine learning models may be trained via supervised training models, unsupervised training models, or both. Supervised training models may include linear regression, logistic regression, support vector machine, the like, or any combination thereof. Unsupervised training models may include hierarchical clustering, k-means, and the self-organizing map, the like, or a combination thereof. The resulting data insights from the data analytics model may enable a feature extraction model. A feature extraction model may allow for specific features to be isolated and extracted from the resulting data. Isolated and extracted data and features may be saved within one or more databases, such as an extracted features database. The development data management module, data analytics module, or both may break down data for use of training the one or more machine learning models.

Data types to be used for training may include one or more video streams, still images, frames, sound, the like, or a combination thereof. Video streams may be received in one or more video coding formats. One or more video coding formats may include H.264, HEVC, VP8, VP9, the like, or a combination thereof. Video frames, images, or both may be received in one or more image formats. One or more image formats may include .png, .jpeg, .gif, the like, or any combination thereof. Data information in addition to or appended to one or more video streams, still images, frames, sound or the like (e.g., data labels) may include one or more data arrays. Data arrays may include integers, floats, decimals, pixels, NumPy values, text, the like, or a combination thereof. Data labels may be provided from data or manually labeled in a .csv, .txt, or similar file format. For video stream training and/or testing, frames may be obtained at 5 frames per second or greater, about 10 frames per second or greater, about 15 frames per second or greater, or even about 20 frames per second or greater. The video stream may be broken down to about 90 frames per second or less, about 60 frames per second or less, or even about 30 frames per second or less.

The model and feature development module may provide a method for improving and training new and current models. The new and existing models may be machine learning and/or artificial intelligence models. The development testing module may acquire and partition data from one or more databases. The one or more databases may be a development cloud training database, extracted feature database, or both. Partitioned datasets may be labeled. Labeling may be manual, automatic, or both. Labeling may include a format, type of data, associated health condition and/or health event to a record, demographic information related to users within the data, or any combination thereof. Once labeled, data may be stored within a training database.

Model training may occur using the data from the training database. Model training may occur by first acquiring the data from the training database. After acquiring the data, the data may go through a preprocessing step. Preprocessing may be dependent on the type of training model. Deep learning and supervised learning algorithms including but are not limited to linear regression, logistic regression, and Support Vector Machine are used in order to take advantage and utilize all of the potentially available data types within training database. Deep learning or deep neural networks (DNNs) are widely accepted and used by data scientists and engineers to accurately classify the different parts of video frames. DNN preprocessing may involve converting video streams to individual frames and/or acquiring frames within an extraction database. Next, the faces within the frames may be extracted and the extractions' sizes may be standardized for input into the model. The data may be segmented into training and validation datasets with corresponding labels and then are fed through a series of convolution layers with relu activation, pooling layers, and connected to a flatten layer and a fully connected (dense) layer with a SoftMax classifier. DNN model structure can change or be modified in order to improve model performance, including but not limited to adding or subtracting convolution layers, altering the input node sizes, changing the activation functions and/or hyperparameter optimization. Supervised learning may be useful for training on text and/or numerical values. Supervised learning preprocessing involves organization of the training data into rows of input data matched with the corresponding label. Then, feeding the data into one of several supervised learning models, including but not limited to linear regression, logistic regression, and Support Vector Machines. After preprocessing, the model begins to be trained. Model training may take several hours to days for deep neural networks and/or several hours for supervised learning models. Once the model is trained, the model may be evaluated by testing individual frames and/or data rows and verifying the performance. The model and feature development module may provide for a useable system with tested models. Once a sufficient model has been trained and evaluated, the model may be configured for test use, saved in a model database, or both. Poor model performance causes prediction and detection inaccuracies, which integers with the main intention for this invention.

The development testing module may provide for rigorous testing of new and existing models. The development testing module is substantially similar to the model and feature development module. The development testing module includes partitioning one or more training datasets, labeling data, storing data within a testing database, acquiring the data from the testing database, data preprocessing, training the model, evaluating the results, the like, or a combination thereof.

The system may include one or more modules. The one or more modules may refer to hardware, software, or both. Modules may be physical components within the system. Modules may be processes executable by one or more processors and stored within one or more memory storage devices.

Facial Recognition and Monitoring Method ("FRM Method")

The present teachings may provide for a facial recognition and monitoring method (also referred to as "FRM method"). The FRM method may be accessible by, stored within, and/or executed by a recognition device, personal computing device, user interface, cloud computing and data management module, the like, or a combination thereof. The FRM method may be software stored in one or more application layers, cloud storage computing storage, applications of a personal computing device, the like, or a combination thereof. At least a portion of the FRM method may reside outside of the recognition device, be accessible by the recognition device, be located within a cloud-based network, be located within a cloud computing and data management module, or a combination thereof. The entire FRM method may be permanently or temporarily stored within the recognition device, cloud-based network, cloud computing and data management module, the like, or a combination thereof. The FRM method may be executed by an image processing unit of a recognition device, one or more processors of one or more cloud computing modules, the like, or a combination thereof. The FRM method may be particularly useful in identifying one or more users via facial recognition, monitoring the one or more users for the presence of one or more health events, detecting the presence of one or more health events, the like, or a combination thereof. The FRM method may be particularly useful in identifying one or more drivers and/or passengers of a vehicle, detecting the presence of one or more health events of a driver and/or passenger via facial recognition, or both. The FRM method may include a plurality of steps. The FRM method may be automatically executed by the recognition device, one or more image processing units, or both. The FRM method may include one or more of the following steps: video acquisition, preprocessing, face extraction, facial recognition, event generation, the like, or any combination thereof.

The FRM method may be automatically triggered by one or more camera stream inputs, video stream inputs, or both. One or more cameras may have one or more users come into the line of sight of the camera. Upon coming into the line of sight of the camera, a video stream may be commenced. The video stream may be transmitted from the one or more camera modules to one or more image processing units. The one or more image processing units upon receiving a video stream may initiate video acquisition. One or more video streams may also be provided by one or more personal computing devices, web servers and/or browsers, one or more video stream management networks, the like, or a combination thereof. While a recognition device may provide for an integrated and easy-to-use device and system, the ability to process an incoming video stream input from other devices provides flexibility for the FRM system and method.

The FRM method may include video acquisition. Video acquisition may function to collect one or more outputs of one or more sensing devices. Video acquisition may function to collect one or more outputs of one or more cameras. Video acquisition may function to collect one or more images, videos, frames, sounds, the like, or any combination thereof. Video acquisition may function to store one or more incoming video streams for further analysis. Video acquisition may be automatically executed by a recognition device, image processing unit, cloud computing module, cloud computing and data management module, the like, a combination thereof. Video acquisition may be automatically executed by one or more processors of an image processing unit, cloud computing module, or both. Video acquisition may be automatically executed upon a camera stream input being detected, one or more video streams being received by an image processing unit or cloud computing module, or combination thereof. Commencement of video acquisition may trigger a recording service. A recording service may be a process for recording the incoming video stream. A recording service may be a process which includes transferring and storing the incoming video stream within the recognition device, image processing unit, storage medium, remote storage device, cloud network, a device and data management module, the like, or any combination thereof. The incoming video stream may be received from the camera by the image processing unit and transmitted for storage in the storage medium of the image processing unit. The incoming video stream may be received from the camera by the image processing unit and transmitted for storage in a remote storage device, a device and data management module, or both. The incoming video stream may be transmitted for storage by the image processing unit toward the storage medium, remote storage device, device and data management module in any sequence, simultaneously, or a combination thereof. The image processing unit may associate the incoming video stream with one or more identifiers prior to storage. The one or more identifiers may include one or more users, recognition devices, timestamps, geolocations, the like, or any combination thereof. After video acquisition, the FRM method moves on to preprocessing.

The FRM method may include preprocessing. Preprocessing may function to breakdown the incoming video stream into a format which can be further analyzed by the image processing unit. Preprocessing may access an incoming video stream from one or more storage mediums, remote storage devices, device and data management modules, the like, or a combination thereof. Preprocessing may be automatically executed by the one or more processors of the image processing unit, cloud computing module, cloud computing and data management module, the like, a combination thereof. Preprocessing may function to break down the incoming video stream into one or more frames. The video stream may be broken down to a frame rate about equal to or less than a frame rate captured by the camera. The video stream may be broken down to about 5 frames per second or greater, about 10 frames per second or greater, about 15 frames per second or greater, or even about 20 frames per second or greater. The video stream may be broken down to about 90 frames per second or less, about 60 frames per second or less, or even about 30 frames per second or less. The one or more frames may be used by one or more subsequent steps and/or sub-steps of the FRM method. Preprocessing may include initiating model identification, environmental analysis, or both.

The FRM method may include model identification. Model identification may be part of preprocessing. Model identification may function to identify one or more models suitable for face extraction, facial recognition, or both. Model identification may function to identify one or more optimal models for face extraction, facial recognition, or both. During model identification, the image processing unit, cloud computing and data management module, or both may evaluate one or more frames. Based on data from the one or more frames, model identification may determine which models may be used. During model identification, the image processing unit, processor of the recognition device, cloud computing module, cloud computing and data management module, the like, a combination thereof may access and extract one or more models from a remote storage device, cloud-based network, or both; transfer the one or more models to a memory medium; or both. The one remote storage device, cloud network, or both may be accessible via one or more network connections of the recognition device, wired and/or wireless connections of the cloud-based network, or both. The one or more models may then be utilized by the processor of the image processing unit, cloud computing module, cloud computing and data management module, the like, a combination thereof to further the FRM method.

The FRM method may include environmental analysis. Environmental analysis may be part of preprocessing. Environmental analysis may function to reduce and/or remove one or more environmental influences from one or more frames. Environmental influences may include different lighting levels (e.g., illumination), multiple individuals captures in the video stream and associated individual frames, background located behind the individual, pose, scale, distance of the user to the camera, gestures of the user, the like, or any combination thereof. Environmental analysis may be completed before, simultaneous with, or after model identification. Environmental analysis may be completed by an image processing unit of the recognition device, cloud computing module, cloud computing and data management module, the like, a combination thereof. Environmental analysis may be completed by one or more processors of the recognition device, cloud computing module, cloud computing and data management module, the like, or a combination thereof. After preprocessing, the FRM method may move on to face extraction.

The FRM method may include face extraction. Face extraction may function to locate and extract one or more faces and facial data from one or more frames. Face extraction may utilize one or more models identified by model identification. Face extraction may utilize one or more frames after environmental analysis. Face extraction may be completed by an image processing unit of the recognition device. Face extraction may be automatically executed by one or more processors of a recognition device, cloud computing module, cloud computing and data management module, the like, a combination thereof. Face extraction may be automatically executed after preprocessing such that one or more individual frames are available for analysis. Face extraction finds one or more faces within a frame, crops one or more pixels of one or more faces, determines a pose of one or more users, determines and extracts one or more features and/or measurements of one or more faces, or any combination thereof. Face extraction may include face detection, pose detection, facial analysis, the like, or a combination thereof. Face detection, pose detection, and/or facial analysis may be completed simultaneously, in sequence, or any variation. Simultaneous evaluation may allow for face extraction to be completed in a faster time frame. Face detection may allow for a face to first be identified before evaluating for further features.

The FRM method may include face detection. Face detection may be part of face extraction. Face detection may function to find one or more faces within one or more frames. Once identified, the one or more detected faces may have their resolution broken down. Face detection may crop one or more frames upon detection of one or more faces. Face detection may crop a frame such that the image is focused on one or more specific faces, is cropped to a predetermined resolution, is cropped to a predetermined shape, the like, or any combination thereof. Cropping may involve cropping the frame such that the image is focused on the face and background is removed. Cropping may involve cropping the image to a standard shape. A standard shape may be rectangular, square, circular, ovular, the like, or any combination thereof. Cropping may involve cropping the image to a predetermined resolution. An image may be cropped to a resolution equal to or less than capable of capturing by a sensing device (e.g., camera). An image may be cropped to be about 150 pixels or greater, about 200 pixels or greater, or even about 300 pixels or greater in one or more directions (e.g., height and/or width). An image may be cropped to be about 1080 pixels or less, about 720 pixels or less, or even about 640 pixels or less in one or more directions (e.g., height and/or width). Cropping may allow for one or more frames to be evaluated with a consistent size and resolution. Cropping may allow for one or more models to identify and classify the face by one or more models. One or more exemplary models may include deep neural network, cascade classifier algorithm, the like, or a combination thereof.

The FRM method may include pose detection. Pose detection may be part of face extraction. Pose detection may function to determine a position and orientation of one or more faces in one or more frames. Pose detection may calculate one or more degrees, two or more, or three degrees of freedom of a user's head pose. The degrees of freedom may include yaw, pitch, and roll. Pose detection may allow for the FRM method to determine where a user is looking (e.g., the road, a fellow passenger, down and away from the road). Pose detection may allow for the FRM method to determine motion (e.g., change in position) of a user's face over a sequence of frames; compensate for a user's facial position during facial recognition and/or event generation; or both.

The FRM method may include facial analysis. Facial analysis may be part of face extraction. Facial analysis may function to extract one or more features of a user's face from one or more frames. One or more features may include a color, location, measurements, status, or a combination thereof of one or more facial features. One or more facial features may include eyes, ears, nose, mouth, and the like. A status may include open, closed, partially closed, looking away, the like, or a combination thereof. Location may include slant of eyes, up or downtown of lips, arch of eyebrows, the like, or a combination thereof. One or measurements may include eye distance (eye center to eye center), nose width and/or height, lip width and/or height, eye width and/or height, ear distance, ear width and/or height, the like, or a combination thereof. One or more locations and/or measurements of one or more features may allow for one or more changes to be determined over a sequence of frames, a baseline to be determined for a user, or a combination thereof.

The FRM method may include facial recognition. Facial recognition may function to classify one or more faces from one or more frames. Classification may allow for specific features, such as those extracted from facial extracted, to be classified, given a status, or both. A status may be a health event or a regular event. Facial recognition may utilize one or more models identified by model identification. Facial recognition may utilize the extracted faces from face extraction. Facial recognition may be automatically executed by one or more processors of a recognition device, cloud computing module, cloud computing and data management module, the like, a combination thereof. Facial recognition may be automatically executed by an image processing unit, cloud computing module, cloud computing and data management module, the like, or a combination thereof. Facial recognition may be automatically executed after one or more faces and/or facial data are extracted with face extraction. Facial recognition may use one or more arrays, facial landmarks, user data history, frame data, or any combination thereof. Facial recognition may determine one or more statuses of one or more faces, track facial changes of one or more users over a sequence of frames, correct inaccurate detections of a user based on system customization, or any combination thereof. Facial recognition may include full face recognition, partial face recognition, behavior recognition, the like, or a combination thereof.

The FRM method may include full face recognition. Full face recognition may be part of facial recognition. Full face recognition may function to classify a status of one or more features of a face from one or more frames. Full face recognition may include breaking one or more extracted faces from one or more frames into one or more pixel arrays. The one or more pixel arrays may represent one or more orthogonal components of face encoding. The one or more pixel arrays may be used by one or more models. One or more models may include deep neural networks, convolutional neural networks, the like, or any combination thereof. Using the one or more models, the one or more processors of the recognition device determine a status of one or more features of a face.

The FRM method may include partial face recognition. Partial face recognition may be part of facial recognition. Partial face recognition may function to locate one or more facial landmarks, perform measurement change calculations of one or more facial features, determine changes of one or more facial features, or any combination thereof on one or more extracted faces from one or more frames. Partial face recognition may utilize one or more models. The one or more models may accessible from model identification, stored within the cloud network, available from third party frameworks and accessible via the cloud network, the like, or a combination thereof. One or more models may include Dlib, as a third-party framework. Partial face recognition may locate one or more facial landmarks within a face. Facial landmarks may include the inner and outer locations one or more eyebrows; the outer locations of a nasal bridge; the inner, outer, top, and bottom locations of one or more eyes; the centers of one or more pupils; the color of one or more irises; the location of the top of the nose; the outer locations of the top and bottom portions of both left and right nose alars, the outer corners of the mouth; the center of the upper lip, the center of the bottom lip; the bottom of the upper lip; the outer edges of ears; the top and bottom of left and right ears; the like, or a combination thereof. Partial face recognition may determine one or more measurements of and/or between one or more facial landmarks. One or more measurements may from one or more frames may be compared with one or more measurements from one or more other frames. Partial recognition may allow for physical changes in one or more measurements to be identified over a sequence of frames from a video stream.

The FRM method may include behavior recognition. Behavior recognition may be part of facial recognition. Behavior recognition may function to customize data related to a user, provide a baseline of data for facial data of a user, correct inaccurate detections relate to facial data of a user, or any combination thereof. Behavior recognition may allow for determination of emotions, gender, the presence and/or absence of makeup, hairstyle and/or color differences, age progression, the like, or any combination thereof of one or more users. For example, behavior recognition may adapt to recognize a user is wearing no makeup or more makeup than usual. Behavior recognition may recognize that a user is excited, happy, sad, angry, or the like. Behavior recognition may recognize a user is aging over time. Behavior recognition may recognize a hairstyle and/or color difference of a user. Based on behavior recognition, face recognition and partial recognition can be further updated before event generation.

The FRM method may include event generation. Event generation functions to generation frame analysis results from the FRM method. Event generation may transmit one or more frame analysis results to a storage medium, remote storage device, device and data management module, the like, or a combination thereof. Event generation may utilize one or more models identified by model identification. Event generation may utilize one or more outputs from preprocessing, face extraction, facial recognition, or a combination thereof. Event generation may be automatically executed by one or more processors of a recognition device, cloud computing module, cloud computing and data management module, the like, or a combination thereof. Event generation may be automatically executed by an image processing unit, cloud computing module, cloud computing and data management module, the like, or a combination thereof. Event generation may be automatically executed after facial recognition determines one or more classifications, status, facial landmarks, user behaviors, or any combination thereof. Event generation may analyze one or more frames. Event generation may append collected image data to one or more frames, frame sequences, video sequences, or a combination thereof to create frame analysis results. Collected image data may include labeling a frame, labeling a video sequence, labeling a frame sequence, or any combination thereof. Collected image data may include extracting collected data into one or more tables, data frames formats, other applicable formats, the like, or any combination thereof. Analyzed frame results may be analyzed by a decision algorithm to generation an interpretation of the frame analysis results. The interpretation may be the presence and/or absence or an irregular health event, regular event, or both. The interpretation may be identification of the irregular health event, regular event, or both.

The FRM method may include generating one or more notifications. One or more notifications may function to alert one or more predetermined individuals of a user undergoing an irregular health event, regular event, or both. One or more notifications may include one or more push notifications, text messages, phone calls (e.g., automated and/or prerecorded), SMS notifications, the like, or a combination thereof. One or more notifications may be referred to as one or more alerts. One or more predetermined individuals may be on or more individuals selected by a user. A user may store one or more predetermined individuals into the FRM system via one or more applications, personal computing devices, or both. Data saved with respect to a predetermined individual may include a phone number, name, email, the, like, or a combination thereof. One or more notifications may be sent from a personal computing device, the system, physical data center, application, over a network, the like, or any combination thereof. One or more notifications may be initiated by one or more processors, image processing units, cloud computing and data management modules, the like, or a combination thereof.

The FRM method may include identifying and activating one or more response protocols. One or more response protocols may aid in placing the user in a position of safety, removing and/or reducing the risk of harm from other individuals in proximity to the user, or both. One or more response protocols may include notifying one or more emergency services, providing a geolocation of a user, engaging one or more safety protocols of a vehicle, or a combination thereof. One or more safety protocols of a vehicle may include engaging driver assistance technology to aid in maneuvering the vehicle to safety. Safety of the vehicle may include slowing down, braking, stopping, initiating lane control, controlling the acceleration, moving the vehicle to the side of the road, a nearby parking spot (e.g., on-street parking, parking lot), the nearest emergency services location, the like, or a combination thereof. By engaging driver assistance technology, the vehicle may be able to be relatively completely maneuvered without the aid of a human driver. Safety protocols of a vehicle may further include turning on one or more hazard lights, sounding a horn or alarm, the like, or a combination thereof.

Vehicle Integration with Driver Assistance

The recognition device and/or system of the present teachings may be able to be integrated with a vehicle. Integration may allow for an advanced driver assistance system (ADAS) to initiate one or more safety protocols of the vehicle, initiate driver assistance technology of a vehicle, or both. One or more safety protocols of the vehicle may include turning on hazard lights, sounding a horn, sounding an alarm, vibrating a driver's seat, maneuvering the vehicle to safety without assistance from a driver, the like, or any combination thereof.

The recognition device may be in wired or wireless communication with a controller area network (CAN) bus, controller area network controller, or both. Communication with the CAN allows for the recognition device to communicate with the vehicle's electronic control units (ECU). The recognition device may have one or more wired connections. A wired connection may connect with a vehicle's diagnostic link connector (DLC). The diagnostic link connector may also be known as a vehicle's OBD-II connector. The OBD-II may provide direct access to the vehicle's Controller Area Network (CAN) Bus. CAN provides a simple protocol which allows for a vehicle's electronic control units (ECUs) to communicate. Via the CAN Bus, the recognition device is able to communication with the vehicle's ECU.

The recognition device may also use one or more application layers. The one or application layers may allow for the ADAS software to be connected to a CAN controller of the vehicle. The application layer may be provided to a socket layer. The socket layer may connect to a socketCAN. SocketCAN may allow for the custom ADAS software to integrate one or more protocols and kernels alongside a character device driver. One or more protocols may include Protocol Family CAN, protocol family internet, or both. A character device driver may be a default CAN protocol and/or kernel of the vehicle. CAN kernels may be used for managing CAN messages communicated on a CAN bus.

ADAS may use one or more hardware or software standards compatible with one or more programming languages. The hardware or software standards may be OpenXC. The one or more programming languages may include Python. The one or more programming languages may translate proprietary CAN protocols into an easy to read format, translate code into a format understanding by the CAN protocols, or both. The one or more hardware or software standards may allow access to any CAN packet via a typical API (application programming interface).

To initiate ADAS and one or more safety protocols of a vehicle, the recognition device may use its wired connection to the vehicle's DLC to communicate with the vehicle's CAN. The ADAS may use SocketCAN by way of programming language and hardware or software standards to integrate one or more custom protocols and/or kernels with the vehicle's CAN. The programming language may by Python. The hardware or software standards may be OpenXC scripts. ADAS may send CAN protocol packets to the CAN. The CAN protocol packets may function as the vehicle's method of communication. Vial the protocol packets, the ADAS and recognition device may be able to obtain at least partial control of the vehicle and execute one or more safety protocols.

ILLUSTRATIVE EXAMPLES

FIG. 1 illustrates the recognition device 10 integrated into a vehicle 12. The recognition device 10 includes a camera 14. The camera 14 is integrated into a rear-view mirror 16. The camera 14 has a line of sight 18 on a driver 20.

Figure 2A:
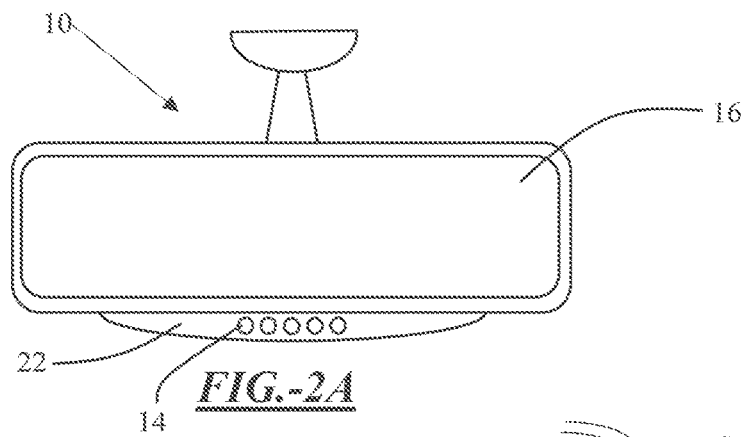
FIG. 2A illustrates a recognition device according to the teachings herein.

FIG. 2A illustrates a recognition device 10. The recognition device 10 includes a rear-view mirror 16. The rear-review mirror 16 includes a camera 14. The camera 14 is integrated into a housing 22 of the rear-view mirror 16.

Figure 2B:
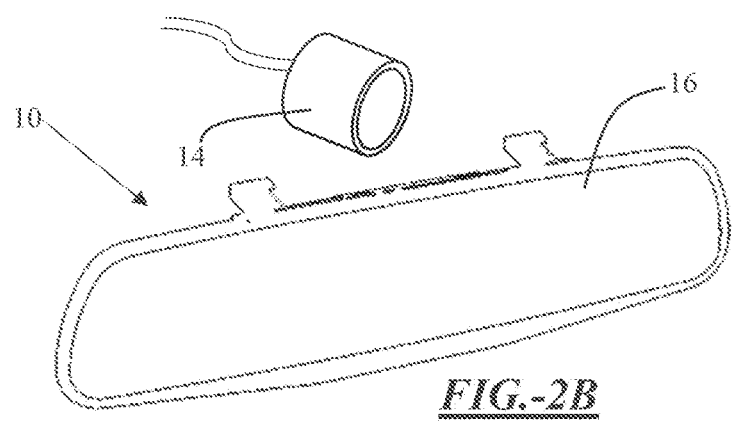
FIG. 2B illustrates a recognition device according to the teachings herein.

FIG. 2B illustrates recognition device 10. The system 10 includes a camera 14. The camera 14 is able to be mounted in proximity to a rear-view mirror 16. The camera 14 can be mounted onto a windshield, headliner, headliner console, and the like to be in proximity of the rear-view mirror 16.

Figure 3:
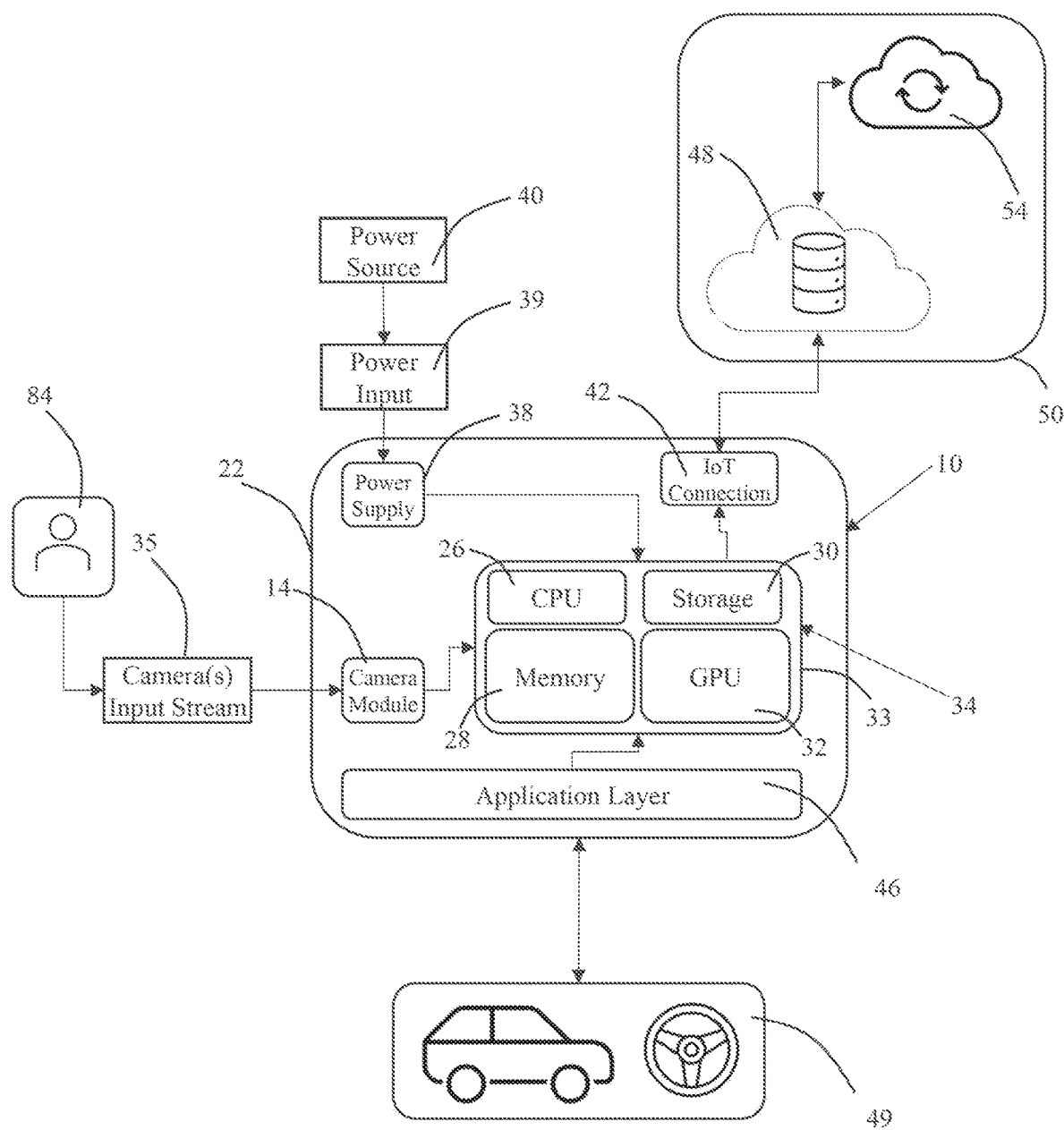
FIG. 3 illustrates a hardware configuration of a recognition device according to the teachings herein.

FIG. 3 illustrates a recognition device 10. The recognition device 10 includes a housing 22. The recognition device 10 includes a camera (e.g., camera module) 14. As an alternative, the camera 14 may be outside of and separate from the housing 22. The camera 14 receives a camera input stream 35. The camera input stream 35 occurs when a user 84 is in view of the camera 14. The camera module 14 is connected to and in communication with an image processing unit 34. The recognition device 10 includes a processor 26, memory medium 28, storage medium 30, and graphics unit processor 32. The image processing unit 34 may include a circuit (e.g., circuit board) 33. The circuit 33 supports and connects the processor 26, memory medium 28, storage medium 30, and graphics unit processor 32. The image processing unit 34 is in electrical communication a power supply 38. The power supply 38 is connected to a power input 39. The power input 39 is connected to a power source 40. The recognition device 10 includes a network connection 42. The network connection 42 may be an IoT connection. The network connection 42 allows for the recognition device 10 to be in communication with a remote storage device 48. The remote storage device 48 is in communication with and part of a network 50. The network 50 also includes a cloud-based network 54. The recognition device 10 includes an application layer 46. The application layer 46 may be part of or accessible by the image processing unit 34. The application layer 46 may include one or more facial recognition and monitoring instructions stored therein which are accessible for execution by the image processing unit 34. The recognition device 10 includes is connected to an advanced driver assistance system 49.

Figure 4:
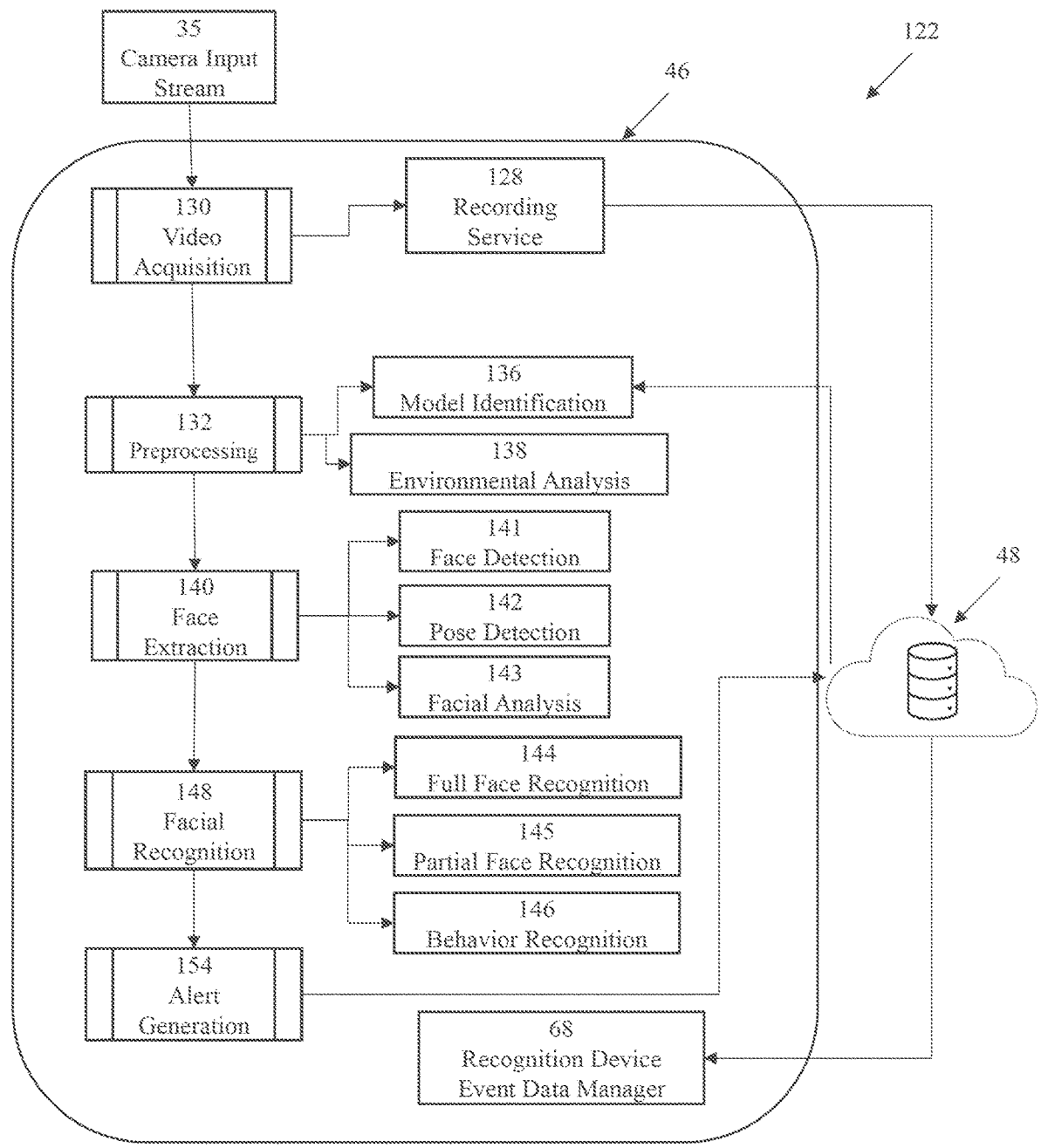
FIG. 4 illustrates a facial recognition and monitoring method executed by a recognition device according to the teachings herein.

FIG. 4 illustrates a method for facial recognition and monitoring 122 of a recognition device 10 (not shown). The method 122 may be part of or stored within an application layer 46. For the method 122 to commence, a camera input stream 35 is received by a camera 14 (not shown). The camera input stream 35 provides the video stream input for the method 122 to commence. Once the camera input stream 35 is received a camera 14 (not shown) and an image processing unit 34, a step of video acquisition 130 takes the video stream input and initiates a recording service 128. The image processing unit 34 executes the recording service 128. The recording service 128 records the video stream input such that the recognition device 10 stores the recorded video stream input in a storage medium 30 (not shown) of the recognition device 10. The recorded video stream input is able to be transferred from the storage medium 30 to the remote storage device 48 (not shown) via a network connection 42 (not shown). The recorded video stream may be able to be transferred from the remote storage device 48 or the storage medium 30 to a cloud-based network 54, such as into a device and data management module 64.

After video acquisition 130, the method moves on to preprocessing 132. During preprocessing 132, the image processing unit 34 passes one or more individual frames from the video stream to a model identification process 136. During the model identification process 136, the image processing unit 34 may decide one or more optimal models to use on the frame for facial extraction and recognition. During the model identification process 136, the image processing unit 34 may load one or more optimal models from a remote storage device 48 to the image processing unit 34, such as into a memory medium 28 (not shown). After, before, or simultaneous with the model identification process 136, an environmental analysis process 138 is initiated. During the environmental analysis 138, the image processing unit 34 reduces and or removes environmental influence from one or more frames of the video stream.

After preprocessing 132, the method moves on to face extraction 140. The one or more individual frames from preprocessing 132 are used for face extraction 140. During face extraction 140, the image processing unit 34 (not shown) detects and extracts faces and/or facial data from one or more frames. The step of face extraction 140 includes sub-steps face detection 141, pose detection 142, and facial analysis 143. During face detection 141, the image processing unit finds one or more faces within the one or more frames. During face detection 141, the image processing may crop one or more pixels making up one or more faces of one or more users. Finding and cropping may allow for one or more deep neural networks to classify the one or more faces. During pose detection 142, the image processing unit may determine bodily position of the one or more users from the one or more frames. Bodily position may include the three degrees of freedom of a user's head, yaw, pitch, and/or roll and represent a position and orientation of a user's face. During facial analysis 143, the image processing unit may extract one or more specific features and/or measurements exhibited by a face of a user within a frame.

After face extraction 140, the method moves on to facial recognition 148. During facial recognition 148, the image processing unit 34 (not shown) uses one or more pre-trained models to classify the one or more faces extracted from the one or more frames. Facial recognition 148 includes sub-steps full face recognition 144, partial face recognition 145, and behavior recognition 146. For full face recognition 144, the image processing unit uses the pixel arrays of the extracted faces from the one or more frames into one or more learning models, which classify the specific features within the face. For partial face recognition 144, the image processing unit uses one or more learning models to locate facial landmarks within the face, performing one or more measurements of the face, and determine one or more changes of the face throughout a sequence of individual frames. For behavior recognition 145, the image processing unit accesses a user's data history and data from one or more individual frames, corrects inaccurate detections of a user, provides a level of customization relative to the user.

After facial recognition 148, the method moves to alert generation 154. During alert generation 143, the image processing unit generates one or more analysis results from facial recognition 148. The image processing unit transmits the one or more analysis results to the remote storage device 48, the device and data management module 64, or both. The image processing unit associated analysis results from each individual frame to its specific frame. The analysis results for one or more frames are evaluated by the image processing unit and compiled by a decision algorithm. The decision algorithm determines if a health event is present in a user. Analysis results may also be transmitted to a recognition device event data manager 68.

Figure 5:
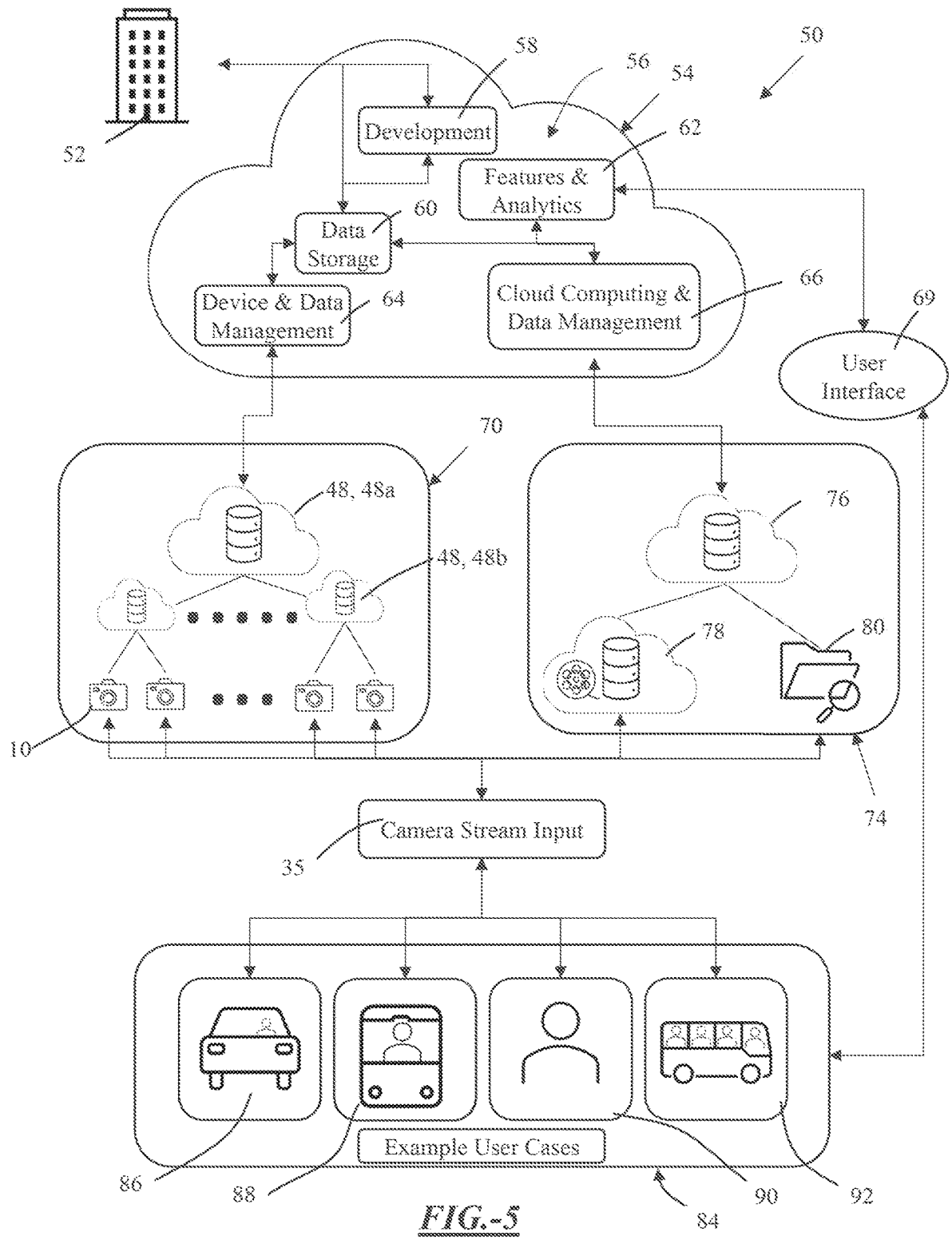
FIG. 5 illustrates a schematic of a facial recognition and monitoring system according to the teachings herein.

FIG. 5 illustrates a schematic (e.g., architecture) of a facial recognition and monitoring system 50 (e.g., system). The system 50 is configured as an overall network. The system 50 includes a physical data center 52. The physical data center 52 hosts a cloud-based network 54. The cloud-based network 54 includes a network architecture 56. The network architecture 56 includes a development module 58, data storage module 60, features and analytics module 62, device and data management module 64, and cloud computing and data management module 66. The cloud-based network 54 is in communication with a user-interface 69.

The cloud-based network 54 is in communication with a recognition device management network 70. The recognition device management network 70 is in communication with the device and data management module 64. The recognition device management network 70 includes one or more remote storage devices 48. The one or more remote storage devices 48 may include one or more main storage devices 48a and one or more node storage devices 48b. One or more recognition devices 10 may be in communication with one or more remote storage devices 48. One or more recognition devices 10 may be in communication with a node storage device 48b.

The cloud-based network 54 is in communication with a video stream management network 74. The video stream management network 74 is in communication with a cloud computing and data management module 66. The video stream management module 74 includes one or more video stream clouds 76. The video stream cloud 76 may be in communication with a user video cloud 78 and a user data center 80.

The recognition device management network 70 and video stream management network 74 may receive a camera stream input 35 from one or more users 84. One or more users 84 may provide a camera stream input 35 into one or more recognition devices 10, user video clouds 78, and/or user data center 80.

The one or more users 84 are illustrated as exemplary use scenarios. The one or more users 84 may include one or more drivers and/or passengers of a private passenger vehicle 86; one or more drivers of public transportation 88; one or more individuals in any setting 90 such as via their mobile device; and one or more passengers in public transportation 90.

Figure 6:
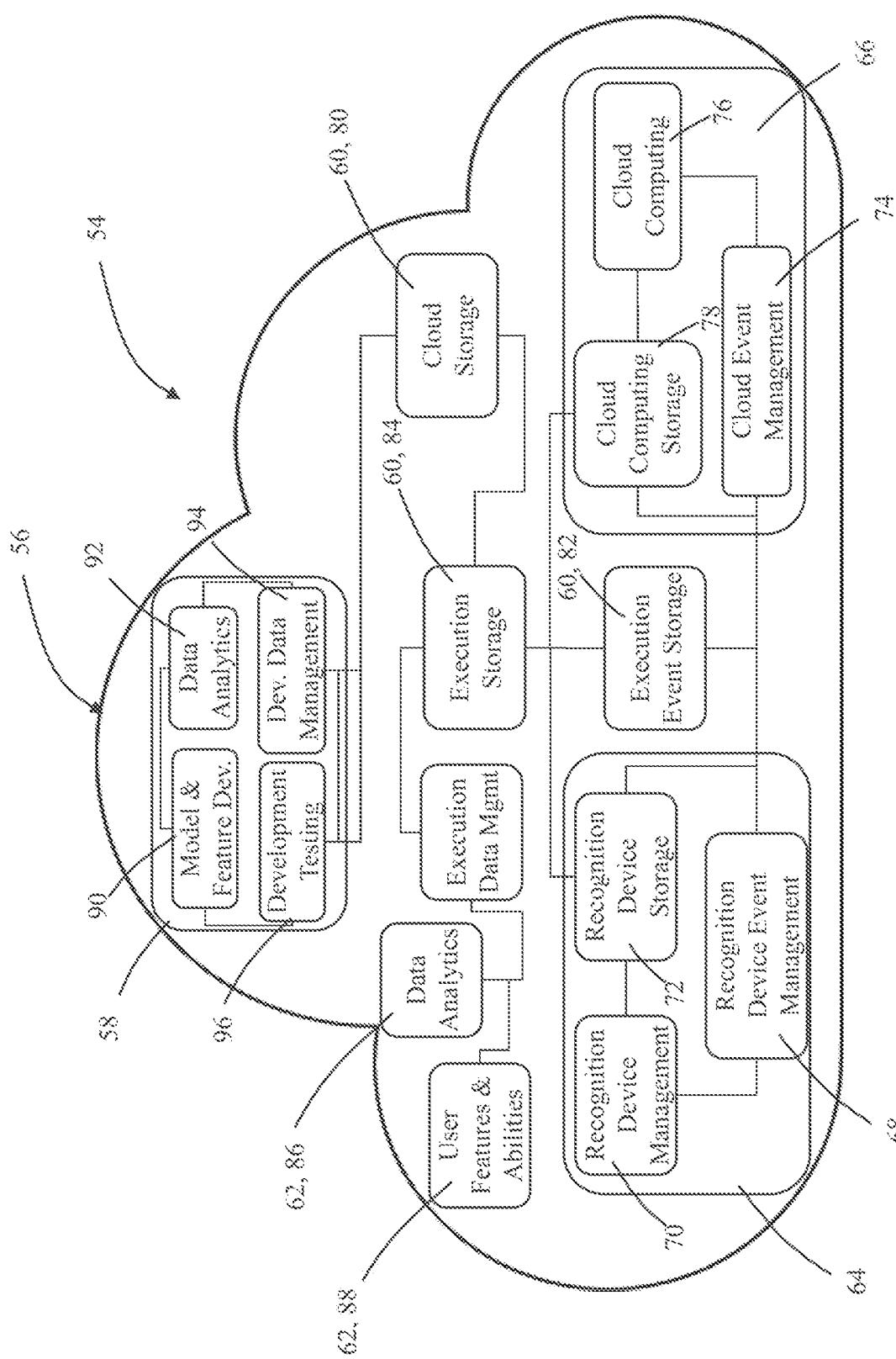
FIG. 6 illustrates the network architecture of the cloud-based network according to the teachings herein.

FIG. 6 illustrates the network architecture 56 of the cloud-based network 54. The cloud-based network 54 includes a development module 58, data storage module 60, features and analytics module 62, device and data management module 64, and cloud computing and data management module 66. The device and data management module 64 includes a device event management sub-module 68, device management sub-module 70, and device storage sub-module 72. The cloud computing and data management module 66 includes a cloud event management sub-module 74, cloud computing sub-module 76, and cloud computing storage sub-module 78.

Data storage module 60 includes cloud storage 80, execution event storage 82, and execution storage 84. The features and analytics module 62 includes a data analytics module 86 and user features and abilities module 88. The development module 58 includes a model and feature development module 90, data analytics module 92, development data management module 94, and development testing module 96.

Figure 7:
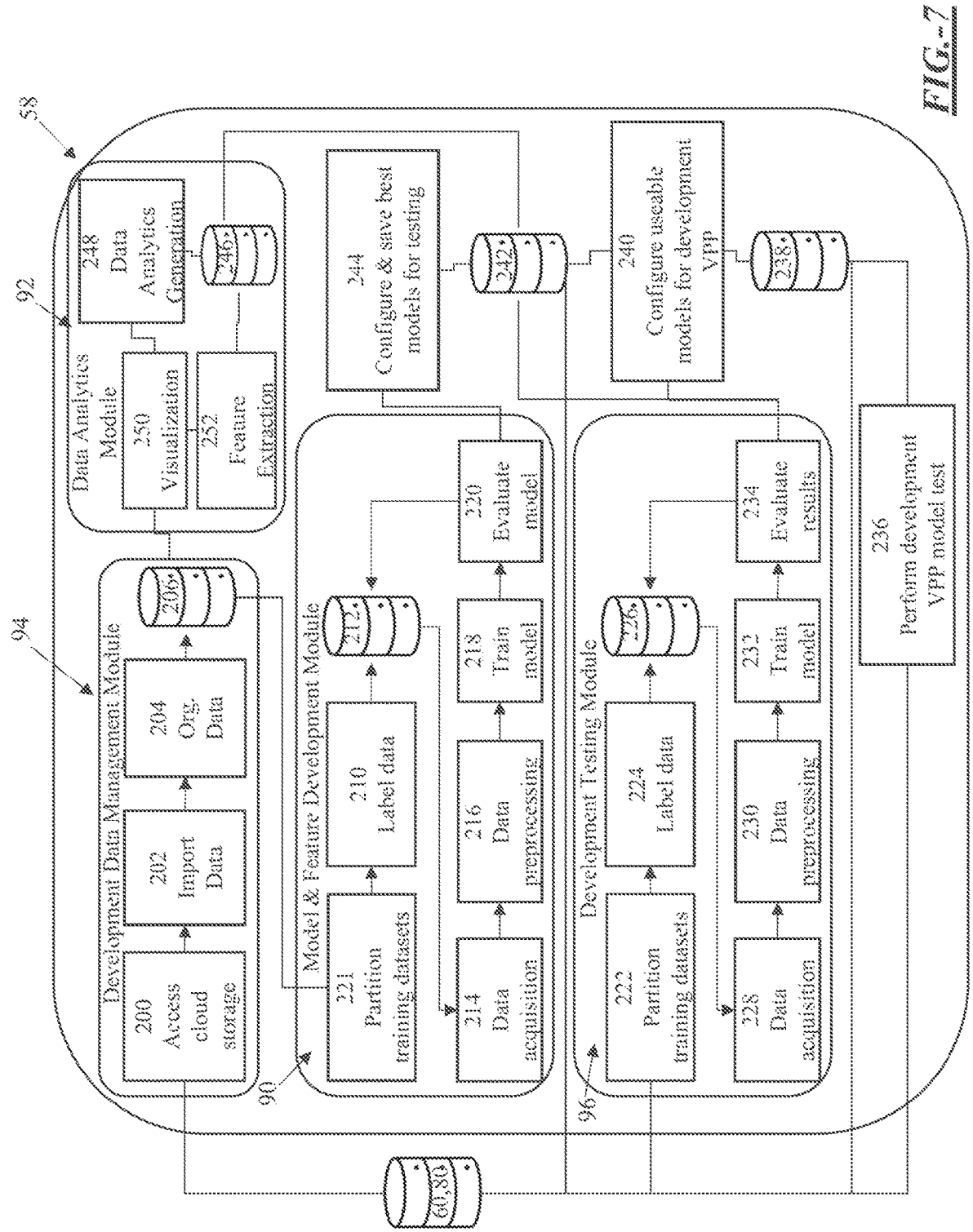
FIG. 7 illustrates a development module according to the teachings herein.

FIG. 7 illustrates a development module 58. The development module 58 enables continuous development improvement and model training for the system 50. The development module 58 includes a model and feature development module 90, data analytics module 92, development data management module 94, and development testing module 96.

Development data management module 94 creates datasets from data stored within cloud storage 60, 80. Development data management accesses cloud storage at step 200. After accessing cloud storage, imports collected data at step 252. After importing, organizes the data for specific feature models to be trained at step 204. After organizing, saves the organized data into a development cloud training database 206. Development data management 240 can also create training datasets from publicly or privately available datasets uploaded to cloud storage 102.

After creation of the database 206, development module 94 transmits the collected and organized datasets to a data analytics module 92. The datasets may be data insights used for developing feature models through the data analytics module 92. The data analytics module 92 enables data visualization through a visualization module 250. The data analytics module 92 generates detailed analytics through a data analytics generation module 248. The data analytics generation module 248 utilized observed data from database 206. The resulting insights from the data analytics generation module 248, enable identification of specific features for isolation and extraction by feature extraction module 252. The one or more specific features which are isolated and extracted are transmitted and stored within an extracted features database 246.

The model and feature development module 90 is a process method for training A.I. and M.L. models. First, data from database 206 is partitioned for model training and validation by collecting applicable training data for the specific feature to be learned, in step 221. Features can be identified from database 246, or by other methods, so as long as training data is sufficient to support model training. Next, datasets are labeled, either manually or by another process, and saved to training database 212. This may be done as a mitigation step in order to maintain a detailed record of the amount, format, and type of data used for training. Model training begins by acquiring data from database 212, in step 214. Next, data preprocessing occurs to correctly format data for the type of model being used, in step 216. Preprocessing depends entirely on the type of training model as multiple data types may be available for training. Deep learning and supervised learning algorithms including but are not limited to linear regression, logistic regression, and Support Vector Machine are used in order to take advantage and utilize all of the potentially available data types within database 212. Following step 216, the model begins training, step 218, which may take several hours to days for DNNs and/or several hours for supervised learning models. Once the model is trained, it can be evaluated by testing individual frames and/or data rows and verifying the performance, at step 220. Model and feature development 90 is an important consideration for creating a useable system 50. Once a sufficient model has been trained and evaluated, the model is configured for test use, at step 244, and saved to a model database 242.

A development testing module 96 allows for rigorous testing of the model performance in order to optimize it for deployment. The development testing module 96 starts by creating and partitioning the testing dataset, step 222, and labeling the data for performance evaluation, step 224. The dataset for testing is saved into a testing database 226, and then imported for use at step 228. The imported data is preprocessed appropriately for the type of model to be tested, step 230. The difference with the model and feature development module is that in preprocessing, the data does not contain the labels (e.g., known outcomes). The model is subsequently fed the testing data, and the outputted predictions, in the form of frames, images, text, numerical values, and/or any other applicable data output, step 232. The predictions are evaluated for accuracy, and the model precision, recall and $F_1$-Score are calculated, step 234. Models that perform well are configured for use in facial recognition and monitoring system, in step 240, and saved to model pipeline testing database 238. Models approved for development testing, are evaluated a facial recognition and monitoring testing and training method.

Figure 8:
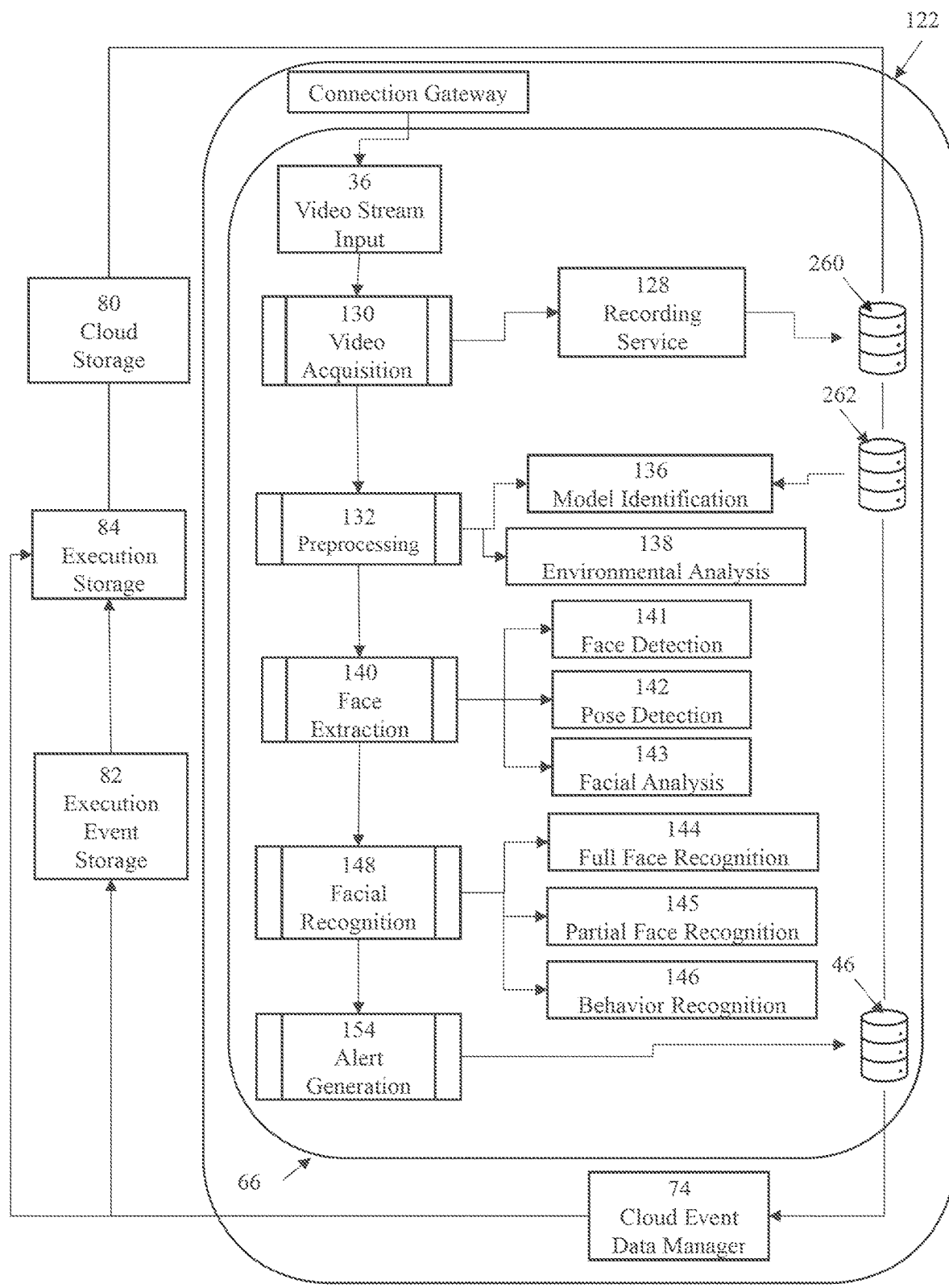
FIG. 8 illustrates a remotely executed facial recognition and monitoring method executed by a cloud-based network according to the teachings herein.

FIG. 8 illustrates a remotely executed method for facial recognition and monitoring 122 (FRM Method). The FRM method 122 may be executed by a cloud-based network 54. The method 122 may be part of or stored within a cloud computing and data management module 66. For the method 122 to commence, a video stream 36 is received by a cloud-based network 54. The video stream is received by a cloud computing and data management module 66. The video stream 36 may be received by a wireless or wired connection gateway. The video stream 36 may be received from one or more remotely located personal computing devise, web servers, video stream management networks, the like, or a combination thereof. The video stream 36 provides the video stream input for the method 122 to commence. Once the video stream 36 is received by a cloud computing and data management module 66, such as an event management module 74, a step of video acquisition 130 takes the video stream input and initiates a recording service 128. The image processing unit 34 executes the recording service 128. The recording service 128 records the video stream input such that the recorded video stream input is stored within a recording database 260. The recording database 260 may be part of the cloud computing and data management module 66. The recorded video stream input is able to be transferred from the recording database 260 to cloud storage 80.

After video acquisition 130, the method moves on to preprocessing 132. During preprocessing 132, the image processing unit 34 passes one or more individual frames from the video stream to a model identification process 136. During the model identification process 136, the cloud computing and data management module 66 may decide one or more optimal models to use on the frame for facial extraction and recognition. During the model identification process 136, one or more optimal models may be accessed from an identified models database 262. After, before, or simultaneous with the model identification process 136, an environmental analysis process 138 is initiated. During the environmental analysis 138, the module 66 reduces and or removes environmental influence from one or more frames of the video stream.

After preprocessing 132, the method moves on to face extraction 140. The one or more individual frames from preprocessing 132 are used for face extraction 140. During face extraction 140, the module 66 detects and extracts faces and/or facial data from one or more frames. The step of face extraction 140 includes sub-steps face detection 141, pose detection 142, and facial analysis 143. During face detection 141, the module 66 finds one or more faces within the one or more frames. During face detection 141, the module 66 may crop one or more pixels making up one or more faces of one or more users. Finding and cropping may allow for one or more deep neural networks to classify the one or more faces. During pose detection 142, the module 66 may determine bodily position of the one or more users from the one or more frames. Bodily position may include the three degrees of freedom of a user's head, yaw, pitch, and/or roll and represent a position and orientation of a user's face. During facial analysis 143, the module 66 may extract one or more specific features and/or measurements exhibited by a face of a user within a frame.

After face extraction 140, the method moves on to facial recognition 148. During facial recognition 148, the module 66 uses one or more pre-trained models to classify the one or more faces extracted from the one or more frames. Facial recognition 148 includes sub-steps full face recognition 144, partial face recognition 145, and behavior recognition 146. For full face recognition 144, the module 66 uses the pixel arrays of the extracted faces from the one or more frames into one or more learning models, which classify the specific features within the face. For partial face recognition 144, the module 66 uses one or more learning models to locate facial landmarks within the face, performing one or more measurements of the face, and determine one or more changes of the face throughout a sequence of individual frames. For behavior recognition 145, the module 66 accesses a user's data history and data from one or more individual frames, corrects inaccurate detections of a user, provides a level of customization relative to the user.

After facial recognition 148, the method moves to alert generation 154. During alert generation 143, the module 66 generates one or more analysis results from facial recognition 148. The module 66 transmits the one or more analysis results to a cloud computing database 264. The cloud computing database 264 may be located within cloud computing storage 78. The module 66 associates analysis results from each individual frame to its specific frame. The analysis results for one or more frames are evaluated by the module 66 and compiled by a decision algorithm. The decision algorithm determines if a health event is present in a user. Analysis results may also be transmitted to a user interface 69 via an event manager 74. One or more steps of the method 122 may be executed by cloud computing 76 (such as shown in FIG. 6). Cloud computing 76 may include one or more processors. The method 122 may be stored within cloud computing storage 78 and accessed by the one or more processors.

Figure 9:
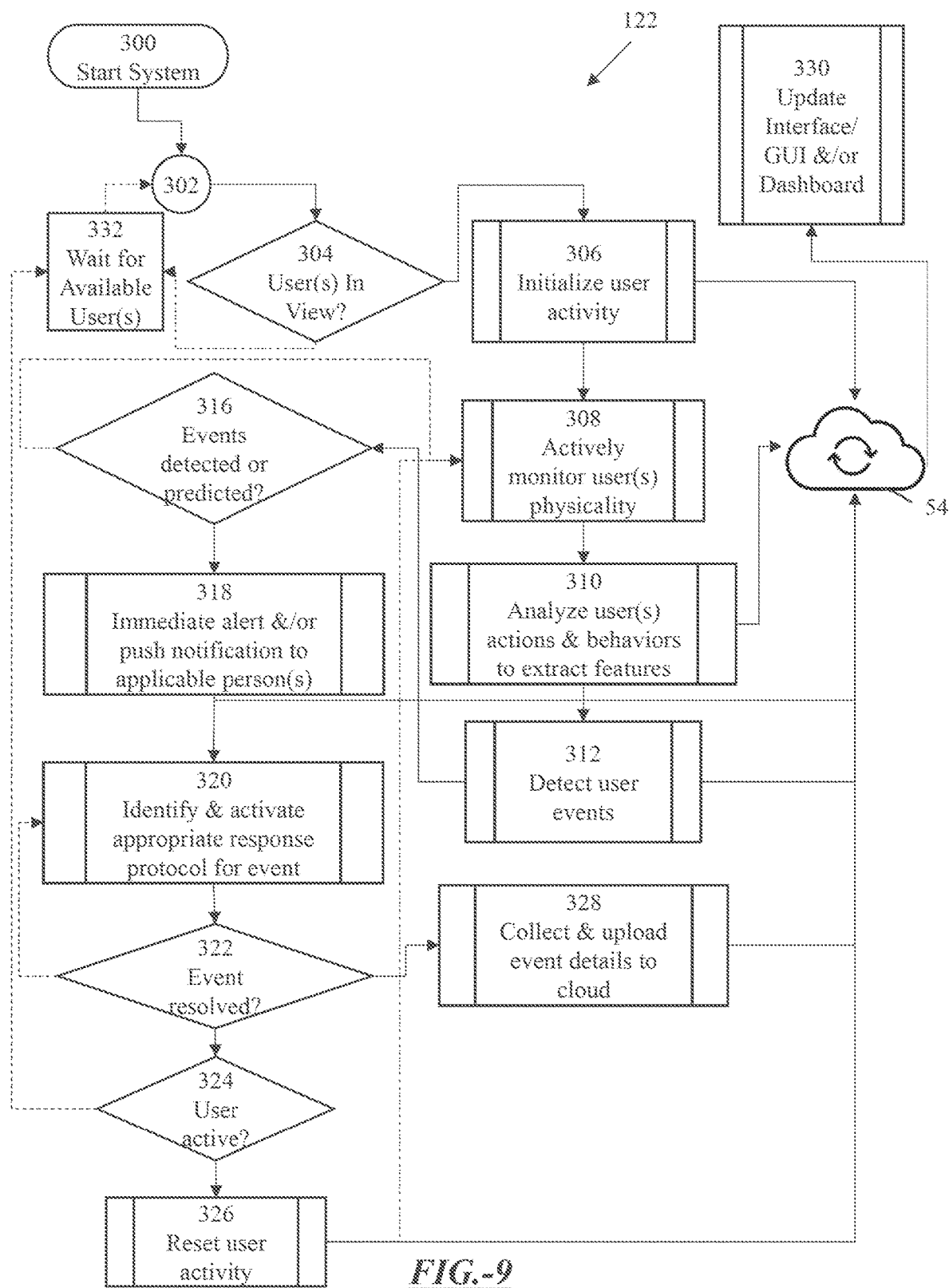
FIG. 9 illustrates a method for facial recognition and monitoring for the presence of a health event according to the teachings herein.

FIG. 9 illustrates a method 122 for facial recognition and monitoring for presence of a health event. The method 122 starts and waits for user(s) to come into view for monitoring 302. When method 122 detects user(s) in view 304 of applicable camera(s) and/or additional sensor(s) and/or receives a video stream 36 (not shown), users are initialized at step 306 into the system. Initializing begins by using facial recognition models to tag each user actively being monitored. By identifying the users, the system is able to differentiate between users. The method 122 then begins to actively monitor each user's physicality at step 308. As the system monitors each user, the system also analyzes each user's actions and behaviors, and extracting applicable features from video frames at step 310. This extraction is accomplished by using the FRM method 122 as illustrated in FIGS. 4 and 8, and a network 50 such as described in FIGS. 5 and 6. After extraction and analysis 310, the method 122 subsequently updates collected data for future use at cloud 54. Based on the collected data, the system generates detections and predictions so as to accurately identify one or more irregular user events (e.g., abnormal health conditions) actively occurring, done at step 312. The detections and predictions from step 312 are transmitted and updated within the cloud 54. As the cloud 54 receives updates, the cloud 54 updates relevant data to a user interface at step 330. The method continues to update the user interface as updated user data, detections, and predictions are collected throughout the method 198.

If the method 122 does not detect a health event, the method 122 repeats a monitoring loop until the one or more users have exited from view. If the method 122 does detect a health event actively occurring or recently occurred in one or more users at step 316, an immediate alert and/or push notification 318 is transmitted to one or more applicable persons. Simultaneous with sending the alert and/or push notification, the collected data is transmitted to the cloud 54.

The method 54 continues by classifying the type of health event occurring, having occurred, or that will occur and activating an appropriate response protocol configured based on the irregular event detected at step 320. If response actions at step 320 resolved the health event, the method collects and transmits all data, features, and/or relevant materials to cloud 54, at step 328. If the event is not resolved, the method 122 returns to step 320 for additional response protocol actions.

When the irregular event is identified as resolved, the method 122 checks the user's activity status at step 324 to determine if monitoring can continue. If the user's status returns to active reset user's status and event details at step 326 and begin new monitoring loop at step 318. If not, method 122 returns to step 332 and awaits new user(s) and/or system shutdown.

Figure 10:
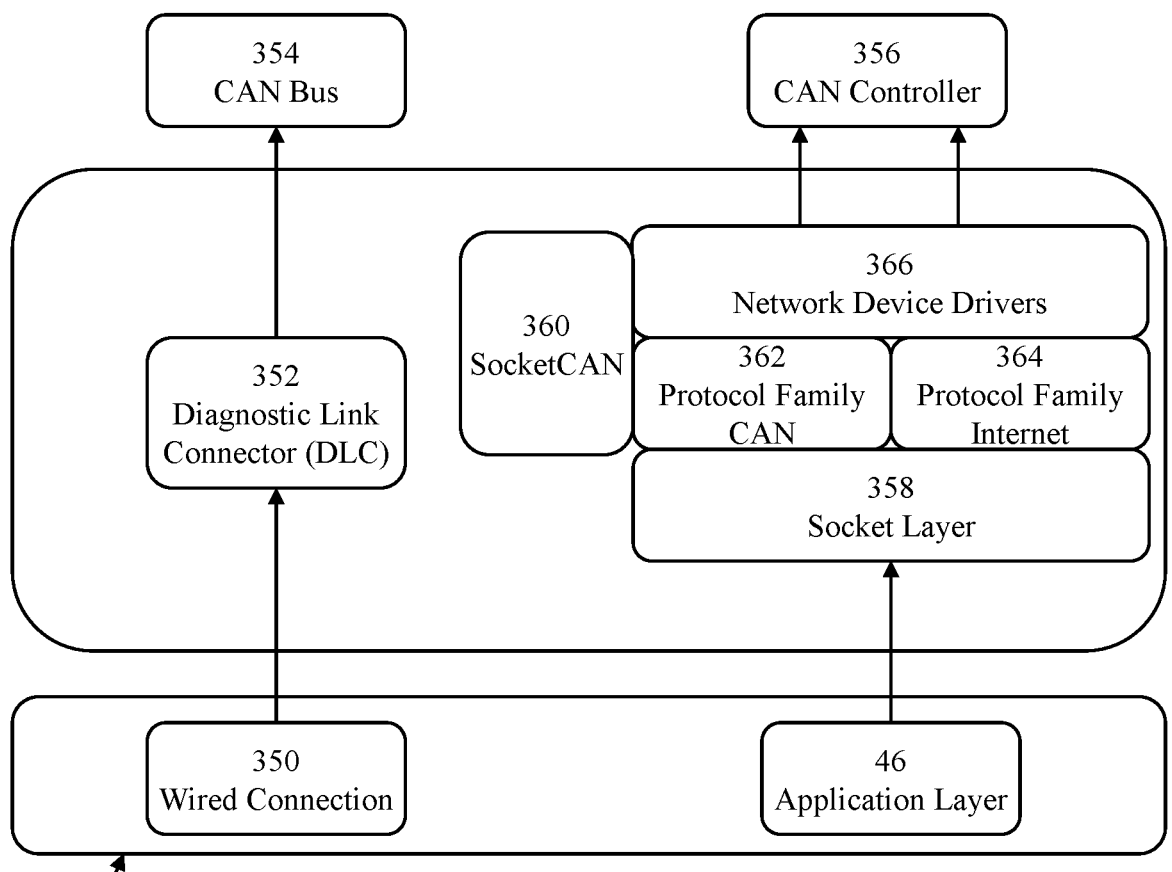
FIG. 10 illustrates an advanced driver assistance system integrated with a vehicle according to the teachings herein.

FIG. 10 illustrates an advanced driver assistance system (ADAS) 49 integrated with a vehicle. ADAS 49 uses a wired connection 350 to a vehicles diagnostic link connector (DLC) 352. The diagnostic link connector 352 provides direct access to a vehicle's Controller Area Network (CAN) bus 354.

ADAS 49 uses an application layer 46. The application layer connects the customized ADAS software 49 to the CAN controller 356. The connection is made through a socket connection 358 to SocketCAN 360. SocketCAN 360 allows for integrating with protocols 362, 364 and kernels 366 alongside the character device driver.

Figure 11:
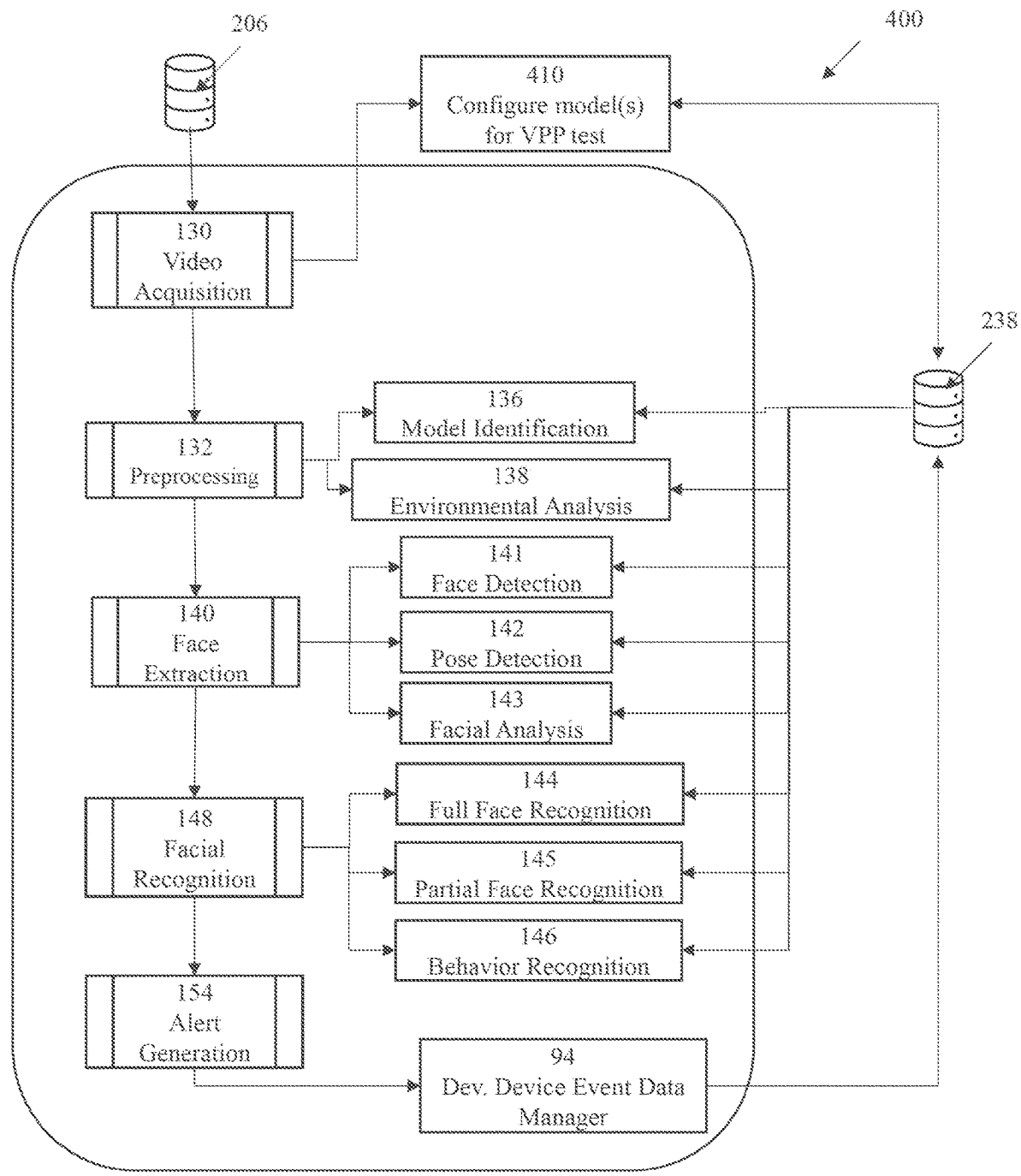
FIG. 11 illustrates a model testing and training method according to the teachings herein.

FIG. 11 illustrates a model testing and training method 400. The model testing and training method 400 is used before a model may be deployed for use, test the model in a production-like execution environment, or both. Module 410 allows a specific model to be configured for model testing and training for the FRM method. This is done by removing a current model, an/or adding the new model for testing by way of database 238. Applicable modules for configuration include model identification 136, environmental analysis 138, face detection 141, pose detection 142, facial analysis 143, full face recognition 144, partial face recognition 145, behavior recognition 146, alert generation 154 or any combination thereof. Following test model configuration and setup, testing data, in the form of a video stream, is obtained from database 2016 and inputted into video acquisition 130. Then, preprocessing 132 passes individual frames to model identification 136, which enables test model to be used, and loads said model from database 238. Next, environmental analysis 138, as previously described in figures above, is performed to identify and mitigate environmental influences within the frame.

Face extraction 140 utilizes face detection 141 to find and extract the pixel representations of the user's face within the frame, and to upload performance to database 238. Pose detection 142 is used to calculate the three degrees of freedom of a user's head pose: yaw, pitch, and roll, representing the position and orientation of the user's face, and to upload performance to database 238. And finally, facial analysis 143 is used to extract one or more specific features and/or measurements exhibited by the user's face in the frame, and to upload performance to database 238.

Facial recognition 148 uses its pre-trained models to classify the face(s) extracted from the frame, and to upload performance to database 238. Full facial recognition 711 feeds the pixel arrays of the extracted faces from the frame into machine learning models (e.g., DNN and CNN models) to classify the status of specific features within the face, and to upload performance to database 238. Partial recognition 145 uses models from third-party frameworks, such as Dlib, to locate the facial landmarks within the face, and perform several types of distance calculations to track a user's physical face changes between the frames of the video stream, and to upload performance to database 238. And finally, behavior recognition 146 utilizes a user's data history and relevant frame data to correct inaccurate detections specific for a user, and to upload performance to database 238.

Following module 148, frame analysis results are generated by module 154, and stored into database 238, as well as updated to cloud storage 206 by module 94 for saving the model performance in order to compare tested models and identify the most optimal configuration.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The terms "generally" or "substantially" to describe angular measurements may mean about +/−10° or less, about +/−5° or less, or even about +/−1° or less. The terms "generally" or "substantially" to describe angular measurements may mean about +/−0.01° or greater, about +/−0.1° or greater, or even about +/−0.5° or greater. The terms "generally" or "substantially" to describe linear measurements, percentages, or ratios may mean about +/−10% or less, about +/−5% or less, or even about +/−1% or less. The terms "generally" or "substantially" to describe linear measurements, percentages, or ratios may mean about +/−0.01% or greater, about +/−0.1% or greater, or even about +/−0.5% or greater.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A method for recognizing and monitoring one or more users for an occurrence of a health event of the one or more users comprising:
   a) detecting the one or more users coming into view of one or more image sensors and receiving video data related to the one or more users, wherein the one or more image sensors are in communication with one or more processors;
   b) receiving the video data by the one or more processors from the one or more image sensors related to the one or more users upon the detecting of the one or more users coming into view of the one or more image sensors;
   c) preprocessing the video data by the one or more processors into frame data, wherein the frame data includes one or more single, batches, sequences or a combination thereof of frames;
   d) extracting facial data by the one or more processors from the frame data to identify the one or more users, wherein the facial data includes one or more extracted faces, one or more numeric array representations of one or more faces of the one or more users, one or more measurements and/or one or more predictions of one or more poses of the one or more users, or a combination thereof;
   e) determining a presence, a probability, and/or an absence of the health event in the one or more users by the one or more processors by comparing the facial data with one or more stored facial data models accessible by the one or more processors;
   f) generating one or more notifications based on recognizing the presence, the probability, or both of the health event or not generating the one or more notifications based on the absence of the health event;
   wherein the method includes the one or more processors continuing to receive the video data while the one or more users are in view of the one or more image sensors, and
   wherein the health event includes one or more irregular health events which include the one or more users experiencing a seizure, a heart attack, a stroke, fainting, vomiting, or a combination thereof;
   wherein the one or more store facial data models includes a plurality of facial data which is pre-stored within one or more non-transitory storage mediums and already associated with one or more irregular health conditions which are associated with the one or more irregular health events; and
   wherein the one or more stored facial data models are determined using supervised machine learning in which the plurality of facial data is stored and associated with the one or more irregular health conditions.

2. The method of claim 1, wherein the video data includes one or more video files, image files, frames, or any combination thereof.

3. The method of claim 2, wherein the video data is received by a recording service module and associated with one or more identification data; and
   wherein the one or more identification data includes one or more video labels, timestamps, camera identifiers, user identifiers, or any combination thereof.

4. The method of claim 2, wherein the video data is transmitted to one or more remotely located non-transitory storage mediums.

5. The method of claim 1, wherein extracting the facial data includes utilizing one or more face detection models, pose detection models, facial analysis models, or a combination thereof.

6. The method of claim 5, wherein the one or more face detection models convert facial image data into the one or more numeric array representations of the one or more faces of the one or more users.

7. The method of claim 5, wherein the one or more pose detection models convert facial image data into the one or more measurements, predictions, or both related to one or more facial poses, body poses, or both of the one or more users.

8. The method of claim 1, wherein the one or more stored facial data models are determined by one or more machine learning networks.

9. The method of claim 8, wherein the one or more machine learning networks include one or more convolutional neural networks (CNN), one or more Dlib machine learning algorithms, or any combination thereof.

10. The method of claim 1, wherein the one or more notifications notifiers includes one or more hazard lights of a vehicle.

11. The method of claim 1, wherein the one or more notifications includes one or more calls to one or more emergency services.

12. The method of claim 1, wherein the one or more notifications includes one or more calls, text notifications, or both to one or more pre-determined individuals.

13. The method of claim 1, wherein the one or more image sensors are part of one or more cameras.

14. The method of claim 1, wherein the one or more image sensors are located in a same device as, remote from, or both the one or more processors.

15. The method of claim 1, wherein upon detecting the presence and/or the probability of the health event, the method includes identifying and activating one or more response protocols.

16. A system for facial recognition and monitoring for performing the method of claim 1, comprising a recognition device including:
   i) one or more cameras having the one or more image sensors; and
   ii) one or more image processing units in communication with the one or more cameras including:
      a) the one or more processors,
      b) one or more graphics processors,
      c) the one or more non-transitory storage mediums, and
      d) one or more internet connections.

17. The system of claim 16, wherein the recognition device is integrated into a vehicle; and
   wherein the one or more cameras are configured to have a line of sight on one or more drivers, one or more passengers, or both within the vehicle.

18. The method of claim 1, wherein the method includes upon recognizing the presence and/or the probability of the health event, transmitting one or more emergency signals from the one or more processors to a vehicle to enable one or more safety protocols including initiating a driver assistance technology to control driving of the vehicle in which the one or more users are located, such that the vehicle drives to and reaches a safe parking destination and/or turns on one or more emergency notifiers of the vehicle.

19. A method for recognizing and monitoring one or more users for an occurrence of a health event of the one or more users comprising:
   a) detecting the one or more users coming into view of one or more image sensors and receiving video data related to the one or more users, wherein the one or more image sensors are in communication with one or more processors;
   b) receiving the video data by the one or more processors from the one or more image sensors related to the one or more users upon the detecting of the one or more users coming into view of the one or more image sensors;
   c) preprocessing the video data by the one or more processors into frame data, wherein the frame data includes one or more single, batches, sequences or a combination thereof of frames;
   d) extracting facial data by the one or more processors from the frame data to identify the one or more users, wherein the facial data includes one or more extracted faces, one or more numeric array representations of one or more faces of the one or more users, one or more measurements and/or one or more predictions of one or more poses of the one or more users, or a combination thereof;
   e) determining a presence, a probability, and/or an absence of the health event in the one or more users by the one or more processors by comparing the facial data with one or more stored facial data models accessible by the one or more processors;
   f) generating one or more notifications based on recognizing the presence, the probability, or both of the health event or not generating the one or more notifications based on the absence of the health event; and
   g) upon recognizing the presence and/or the probability of the health event, transmitting the one or more emergency signals from the one or more processors to a vehicle to enable one or more safety protocols including initiating a driver assistance technology to control driving of the vehicle in which the one or more users are located, such that the vehicle drives to and reaches a safe parking destination and/or turns on one or more emergency notifiers of the vehicle; and
   wherein the method includes the one or more processors continuing to receive the video data while the one or more users are in view of the one or more image sensors;
   wherein the health event includes one or more irregular health events which include the one or more users experiencing a seizure, a heart attack, a stroke, fainting, vomiting, or a combination thereof;
   wherein the one or more stored facial data models are determined by one or more machine learning networks;
   wherein the one or more machine learning networks include one or more convolutional neural networks (CNN), one or more Dlib machine learning algorithms, or any combination thereof;
   wherein the one or more stored facial data models includes a plurality of facial data which is pre-stored within one or more non-transitory storage mediums and already associated with one or more irregular health conditions which are associated with the one or more irregular health events; and
   wherein the one or more stored facial data models are determined using supervised machine learning in which the plurality of facial data is stored and associated with the one or more irregular health conditions;
   wherein extracting the facial data includes utilizing one or more face detection models, pose detection models, facial analysis models, or a combination thereof;
   wherein the one or more face detection models convert facial image data into the one or more numeric array representations of faces of the one or more users; and
   wherein the one or more pose detection models convert the facial image data into one or more measurements, predictions, or both related to one or more facial poses, body poses, or both of the one or more users.

20. The method of claim 19, wherein the one or more emergency notifiers includes one or more hazard lights of the vehicle;
   wherein the one or more notifications includes one or more calls to one or more emergency services; and
   wherein the one or more notifications includes one or more calls, text notifications, or both to one or more pre-determined individuals.

* * * * *